US009149599B2

(12) United States Patent
Walter et al.

(10) Patent No.: US 9,149,599 B2
(45) Date of Patent: Oct. 6, 2015

(54) BRAIN STIMULATION SYSTEMS AND METHODS

(75) Inventors: Timothy J. Walter, Upper Arlington, OH (US); Uma Marar, Blacklick, OH (US)

(73) Assignee: Lotus Magnus, LLC, Grove City, OH (US)

( * ) Notice: Subject to any disclaimer, the term of this patent is extended or adjusted under 35 U.S.C. 154(b) by 594 days.

(21) Appl. No.: 12/514,948

(22) PCT Filed: Oct. 6, 2008

(86) PCT No.: PCT/US2008/078940
§ 371 (c)(1),
(2), (4) Date: May 14, 2009

(87) PCT Pub. No.: WO2009/126179
PCT Pub. Date: Oct. 15, 2009

(65) Prior Publication Data
US 2011/0015469 A1    Jan. 20, 2011

Related U.S. Application Data

(60) Provisional application No. 61/043,513, filed on Apr. 9, 2008.

(51) Int. Cl.
| | | |
|---|---|---|
| *A61B 5/00* | (2006.01) | |
| *A61M 21/02* | (2006.01) | |
| *G09B 19/00* | (2006.01) | |
| *A61B 18/00* | (2006.01) | |
| *A61M 21/00* | (2006.01) | |
| *A61N 5/06* | (2006.01) | |

(52) U.S. Cl.
CPC .............. *A61M 21/02* (2013.01); *A61B 5/4806* (2013.01); *A61B 5/4812* (2013.01); *A61B 2018/00571* (2013.01); *A61M 2021/0016* (2013.01); *A61M 2021/0027* (2013.01); *A61M 2021/0044* (2013.01); *A61M 2205/502* (2013.01); *A61M 2230/10* (2013.01); *A61M 2230/18* (2013.01); *A61M 2230/60* (2013.01); *A61N 2005/0653* (2013.01); *G09B 19/00* (2013.01)

(58) Field of Classification Search
CPC ..................... G09B 19/00; A61B 2018/00571; A62B 5/4812; A62B 5/4806
USPC .................................................. 600/544, 545
See application file for complete search history.

(56) References Cited

U.S. PATENT DOCUMENTS

| | | | |
|---|---|---|---|
| 3,160,159 A | | 12/1964 | Hoody et al. |
| 3,388,699 A | | 6/1968 | Webb et al. |
| 3,495,596 A | | 2/1970 | Condict |
| 5,356,368 A | * | 10/1994 | Monroe .......................... 600/28 |
| 5,551,879 A | * | 9/1996 | Raynie et al. ................. 434/236 |
| 5,601,090 A | * | 2/1997 | Musha .......................... 600/544 |

(Continued)

OTHER PUBLICATIONS

Post Training REMs Coincident Auditory Stimulation Enhances Memory in Humans, Carlyle Smith, Kimberly Weeden; Psychiatric Journal of the University of Ottawa, vol. 15(2), 85-90, Jun. 1990.*

(Continued)

*Primary Examiner* — Etsub Berhanu
*Assistant Examiner* — Karen Toth
(74) *Attorney, Agent, or Firm* — Finala & Weaver P.L.L.C.

(57) ABSTRACT

Systems and methods for brain stimulation.

23 Claims, 17 Drawing Sheets

(56) References Cited

U.S. PATENT DOCUMENTS

| | | | |
|---|---|---|---|
| 5,769,778 A | | 6/1998 | Abrams et al. |
| 5,813,993 A | * | 9/1998 | Kaplan et al. ............... 600/544 |
| 5,954,667 A | | 9/1999 | Finkenzeller et al. |
| 5,999,846 A | | 12/1999 | Pardey et al. |
| 6,052,619 A | | 4/2000 | John |
| 6,161,030 A | | 12/2000 | Levendowski et al. |
| 6,167,298 A | | 12/2000 | Levin |
| 6,230,049 B1 | | 5/2001 | Fischell et al. |
| 6,272,378 B1 | | 8/2001 | Baumgart-Schmitt |
| 6,381,481 B1 | | 4/2002 | Levendowski et al. |
| 6,385,486 B1 | | 5/2002 | John et al. |
| 6,425,852 B1 | | 7/2002 | Epstein et al. |
| 6,496,724 B1 | | 12/2002 | Levendowski et al. |
| 6,497,658 B2 | | 12/2002 | Roizen et al. |
| 6,625,485 B2 | | 9/2003 | Levendowski et al. |
| 6,640,122 B2 | | 10/2003 | Manoli et al. |
| 6,926,660 B2 | | 8/2005 | Miller |
| 6,950,697 B2 | | 9/2005 | Jordan |
| 6,978,179 B1 | | 12/2005 | Flagg et al. |
| 6,984,202 B2 | | 1/2006 | Ashenden |
| 7,024,234 B2 | | 4/2006 | Margulies et al. |
| 7,104,947 B2 | | 9/2006 | Riehl |
| 7,153,256 B2 | | 12/2006 | Riehl et al. |
| 7,223,245 B2 | | 5/2007 | Zoth et al. |
| 7,297,119 B2 | | 11/2007 | Westbrook et al. |
| 2003/0199945 A1 | | 10/2003 | Ciulla |
| 2004/0234103 A1 | | 11/2004 | Steffein |
| 2005/0020934 A1 | | 1/2005 | Potter et al. |
| 2005/0165323 A1 | | 7/2005 | Montgomery et al. |
| 2005/0182287 A1 | | 8/2005 | Becker |
| 2005/0234518 A1 | | 10/2005 | Heruth et al. |
| 2005/0256539 A1 | | 11/2005 | George et al. |
| 2005/0268916 A1 | * | 12/2005 | Mumford et al. ......... 128/207.13 |
| 2005/0277821 A1 | | 12/2005 | Payne, Jr. |
| 2006/0094971 A1 | | 5/2006 | Drew |
| 2006/0106275 A1 | * | 5/2006 | Raniere ............................ 600/26 |
| 2006/0205993 A1 | | 9/2006 | Fischell et al. |
| 2007/0027388 A1 | | 2/2007 | Chou |
| 2007/0287896 A1 | | 12/2007 | Derchak et al. |
| 2008/0071150 A1 | | 3/2008 | Miesel et al. |
| 2008/0081941 A1 | | 4/2008 | Tononi |
| 2008/0146893 A1 | | 6/2008 | Levendowski et al. |
| 2008/0218311 A1 | * | 9/2008 | Pless ............................ 340/5.81 |
| 2012/0251989 A1 | * | 10/2012 | Wetmore et al. ............ 434/236 |
| 2013/0190556 A1 | * | 7/2013 | Wetmore et al. ............. 600/28 |
| 2014/0057232 A1 | * | 2/2014 | Wetmore et al. ............ 434/236 |

OTHER PUBLICATIONS

Maintaining memories during reactivation, Bjorn Rasch and Jan Born, Current Opinion in Neurobiology 2007, 17:698-703.*

Odor Cues During Slow-Wave Sleep Prompt Declarative Memory Consolidation, Bjorn Rasch, Christian Buchel, Steffen Gais, Jan Born; Science, Mar. 9, 2007, vol. 315, 1426-1429.*

Strengthening Individual Memories by Reactivating Them During Sleep, John D. Rudoy, Joel L. Voss, Carmen E. Westerberg, Ken A. Paller; Science, Nov. 20, 2009, vol. 326, 1079.*

Badillo et al., "EEG Digital System for Long Time Recording," Congreso Nacional De Instrumentacion, Memorias Somi XV SIS-0; 6 pgs. Oct. 25, 2002.

"Battery-free, Wireless Encephalogram," [online]. MedGadget, Apr. 14, 2008. [retrieved on Apr. 17, 2008]. Retrieved from the Internet:<URL:http://www.medgadget.com/archives/2008/04/batteryfree_wireless_encephalogram>; 6 pgs.

Bielikova, Maria, "A Body-Monitoring System with EEG and EOG Sensors," ERCIM News No. 51, Oct. 2002 [online]. Available at <http://www.ercim.org/publication/Ercim_News/enw51/bielikova.htm>2 pgs.

Cavuoto, James (Ed.), "Alertness Monitoring Devices Emerge from San Diego," Neurotech Business Report, Oct. 2001. [online]. [retrieved on May 1, 2009]. Available online at <http://www.neurotechreports.com/pages/alertness.html>. 2 pgs.

Church et al., "Evoked K-Complexes and Cardiovascular Responses to Spindle-Synchronous and Spindle-Asychoronous Stimulus Clicks During NREM Sleep," Electroencephalography and Clinical Neurophysiology, 1978;45:443-453.

Huber et al., "TMS-Induced Cortical Potentiation during Wakefulness Locally Increases Slow Wave Activity during Sleep," PloS One, Mar. 2007;3(e276):1-7.

U.S. Appl. No. 12/438,273, filed Feb. 20, 2009, Walter et al.

Marshall et al., "Transcranial Direct Current Stimulation during Sleep Improves Declarative Memory," J of Neuroscience, Nov. 3, 2004; 24(44):9985-9992.

Massimini et al., "Triggering sleep slow waves by transcranial magnetic stimulation," PNAS, May 15, 2007;104(2):8496-8501.

"Pilot Test of Fatigue Management Technologies," Federal Motor Carrier Safety Administration, Feb. 2005. [online]. [retrieved on Mar. 28, 2008]. Available online at <http://www.fmcsa.dot.gov/facts-research/research-technology/tech/PilotTest-of-FatigueManagement-Technologies-031005.htm.> 4 pgs.

Prime et al., "Transcranial Magnetic Stimulation over Posterior Parietal Cortex Disrupts Transsaccadic Memory of Multiple Objects," J Neuroscience, Jul. 2, 2008, 28(27):6938-6949.

Schmidt et al., "Mobile Sleep Diagnostic Devices for Testing around the World," presented at Pan America Health Care Exchange (PAHCE) Feb. 12-16, 2007. Longbeach—Los Angeles, CA. Available online at <http://www.clevemed.com/clevemed_pdfs/Mobile_Sleep_Diagnostic_Devices%20Intl.pdf> 6 pgs.

Smith and Weeden, "Post Training REMs coincident Auditory Stimulation Enhances Memory in Humans," Psychiatr J. Univ Ottawa, Jun. 1990;15(2):85-90.

Tenenbaum, D., "Study puts us one step closer to understanding the function of sleep," [online]. Apr. 30, 2007. [retrieved on Apr. 17, 2008]. Retrieved from the Internet: <URL:http://www.news.wisc.edu/13733>; 3 pgs.

"Wireless EEG Powered by Body Heat," [online]. MedGadget, Oct. 31, 2007. [retrieved on Apr. 17, 2008]. Retrieved from the Internet:<URL:http://www.medgadget.com/archives/2007/10/wireless_eeg_powered_by_body_heat.htm>; 6 pgs.

Antony, et al., "Cued Memory Reactivation During Sleep Influences Skill Learning," Nature Neuroscience, Advanced Online Publication, 2012, pp. 1-3.

Born et al., "System consolidation of memory during sleep," Psychol. Res., 2012; 76(2):192-203.

Rasch, et al., "Odor Cues During Slow-Wave Sleep Prompt Declarative Memory Consolidation," Science, vol. 315, 2007, pp. 1426-1429.

Rudoy, et al., "Strengthening Individual Memories by Reactivating Them During Sleep," Science, vol. 326, 2009, p. 1079.

International Preliminary Report on Patentability and Written Opinion for PCT/US2008/078940; 7 pgs.

* cited by examiner

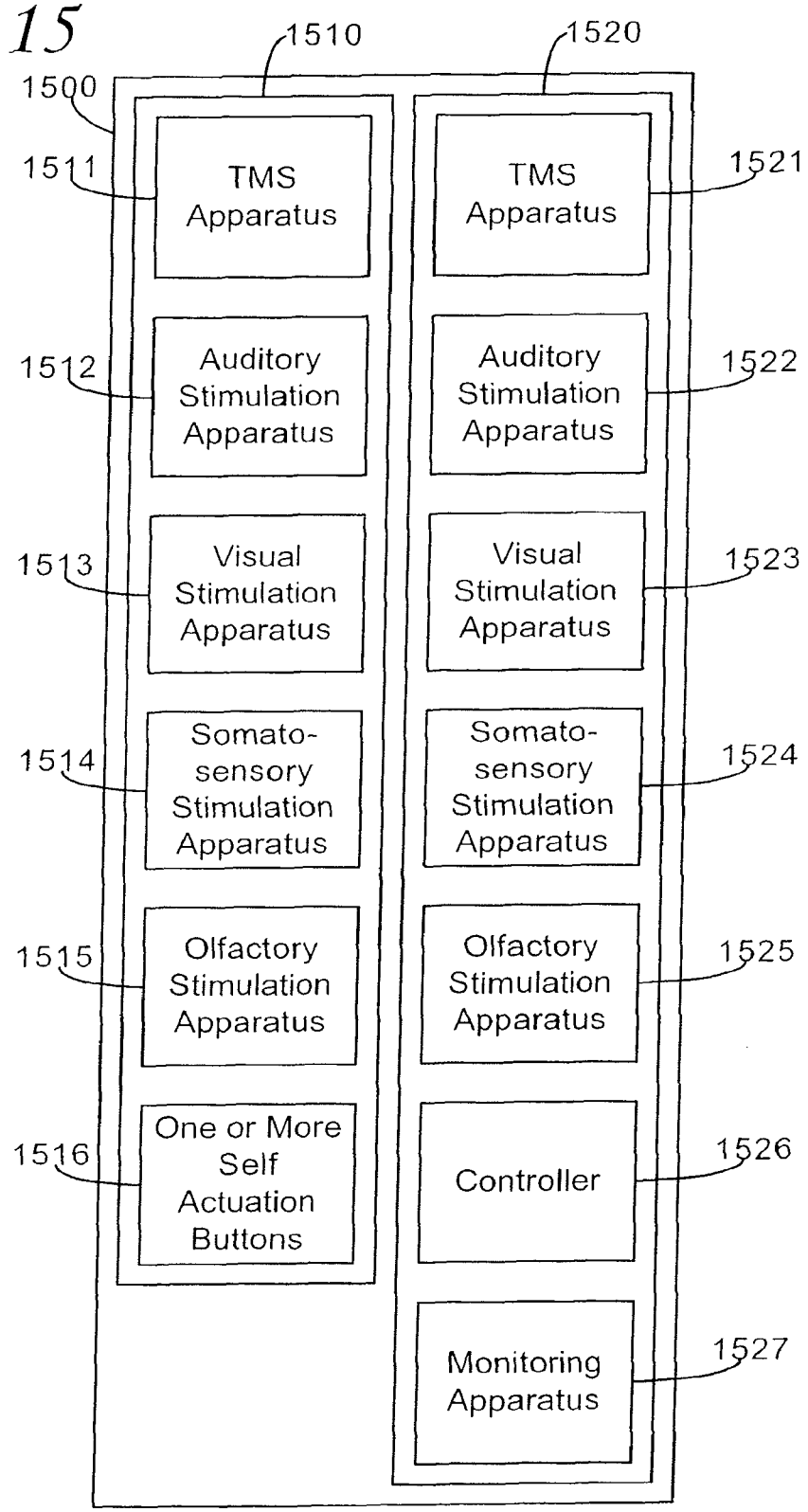

BRAIN STIMULATION SYSTEMS AND METHODS

This application is the §371 U.S. National Stage of International Application No. PCT/US2008/078940, filed Oct. 6, 2008, which claims the benefit of U.S. Provisional Application Ser. No. 61/043,513, filed Apr. 9, 2008, each of which are incorporated by reference herein in their entireties.

The present invention relates generally to brain stimulation systems and methods. More specifically, the present invention relates to systems and methods that may enhance memory consolidation by stimulating neurophysiological events during wakefulness and during sleep.

Electroencephalography (EEG) records the neural activity of electrical potential across cell membranes, which are detected through the cerebral cortex and recorded by a plurality of electrodes. The changes in electrical potential in the cortex contain rhythmical activity, which typically occur at frequencies of about 0.5 to 70 cycles per second (hertz). While awake, fast, random signals are predominantly generated at low voltage and mixed frequency. While asleep, more predictable signals are generated at a low voltage and predictable frequencies over predictable periods.

Five distinct brain wave patterns that are commonly detected during an EEG recording are delta waves (e.g., about 0.5-3 hertz), theta waves (e.g., about 3-8 hertz), alpha waves (e.g., about 8-12 hertz), beta waves (e.g., about 13-38 hertz), and gamma waves (e.g., about 38-70 hertz). Many of these frequencies may be observed in a subject's sleep cycle. A sleep cycle may be defined as a progression of brainwave patterns that may be seen while a subject is sleeping. Generally, subjects undergo several sleep cycles per night, each lasting around ninety minutes. Each progression of brainwave patterns during the sleep cycle may be referred to as a stage of the sleep cycle. Generally, each sleep cycle progresses consecutively through stage I sleep, stage II sleep, stage III sleep, stage IV sleep (stage III sleep and stage IV sleep may be grouped together and referred to as slow wave sleep), briefly back to stage II sleep, and then rapid eye movement (REM) sleep.

During stage I sleep, a subject's brain waves slow in frequency transitioning from alpha waves to theta waves. During stage II sleep, a subject's brain waves slow further and include various bursts of activity such as sleep spindles and K-complexes. Sleep spindles, as seen on an EEG recording, are brain wave patterns that begin low in amplitude and gradually increase amplitude before gradually decreasing over a second or two. Sleep spindles may also be referred to as a crescendo-decrescendo pattern. In general, sleep spindles have a frequency of about 12-14 hertz. K-complexes are brain wave patterns that include large, relatively-slow waves (e.g., 1-2 hertz) and may occur during stage II sleep. During stage III sleep, a subject's brain waves slow further in frequency and may be defined by a period in which delta waves are less than 50 percent of the total wave patterns. During stage IV sleep, a subject's brain waves slow further still and may be defined by period in which delta waves make up between 20 and 50 percent of the wave patterns. During REM sleep, a subject's brain waves increase in frequency to the gamma frequency similar to the brain waves observed during waking consciousness.

Further, during REM sleep, various bursts of sawtooth waves may be observed. The sawtooth waves that may be seen during REM sleep may precede a burst of rapid eye movements. Sawtooth waves, as seen on an EEG recording, look like a series of shark fins that oscillate at the theta frequency. Although REM sleep is characterized by actual rapid eye movement, periods of little to no eye movements may occur during REM sleep (tonic REM), which are then punctuated by bursts of rapid eye movement (phasic REM).

Waking consciousness is generally experienced neurophysiologically at a brainwave frequency of about forty hertz. The amygdala is part of the limbic system that judges emotional relevance of an experience. When the amygdala and/or the rest of the limbic system experience an event that has enough emotional relevance, the event is temporarily stored in the hippocampus. A subject's brain hippocampal wave frequency is generally about 3-8 hertz (the theta frequency) when such events are temporarily stored in the hippocampus.

Electrooculography (EOG) records the ocular activity of the electrical potential from the retina, which consists of an electrically-charged nerve membrane. EOG signals can be measured by placing electrodes near an eye. Motion of an eye may cause a measurable change of electrical potential between two or more surface electrodes.

Electromyography (EMG) records the muscular activity of electrical potential across muscular membranes, which range between about 50 microvolts to about 300 millivolts (depending on the muscle under observation). Typical repetition rate of muscle unit firing is about 7 hertz to about 200 hertz, depending on the size of the muscle, the type of muscle, etc. EMG signals may be recorded within a muscle (i.e., intramuscular EMG) or on the surface a subject's skin outside of a muscle.

A subject's EOG and/or EMG may also be useful in determining the sleep cycle of a subject. For example, when phasic burst of EOG eye movements are seen during low EMG activity along with simultaneous low voltage, mixed frequency EEG activity, the subject is likely to be in REM sleep.

Physical tasks (e.g., trampolining), learning tasks (e.g., learning a foreign language or learning Morse code), and visual tasks (e.g., visual field inversion or visual discrimination tasks) have been shown to demonstrate increases in REM sleep following successful learning. Brain wave recordings in animals have shown that the same brain areas that are activated during learning while awake are again activated during that night's REM sleep. For example, the brain wave frequency recorded in the hippocampus of rats while learning "wheel running" is in the theta frequency. The same brainwave pattern and frequency, i.e., the theta frequency, may be seen the hippocampus of the same rats during subsequent slow wave sleep and then during subsequent REM sleep. Further, this correlation has also been witnessed in rats performing other learning behavior, such as running wheels and mazes, and in other animals, such as zebra finches as they are learning and rehearsing songs.

Transcranial electric stimulation (TES) may deliver electrical current stimulation to the brain. When TES is used through the scalp to stimulate the frontal lobes during slow wave sleep over thirty minute periods, memory word pairs learning during wakefulness may be improved. It was concluded that the effects of transcranial direct cortical stimulation enhanced the generation of slow waves and thus facilitated the processes of neuronal plasticity.

Performance of a simple finger-tapping task was, in one study, improved by about twenty percent if the subjects were allowed a night of sleep between training and retesting. Further, high correlation existed between post-sleep performance and the amount of stage II sleep obtained in the last quarter of the sleep night.

Subjects tested on a series of procedural motor tasks, e.g., a pursuit rotor task, a motor task involving dexterity with a ball and cup, a direct trace task, and the fine manual dexterity game "Operation," have been shown to have an increase in the total number of stage II sleep spindles. Subjects that were not exposed to the tasks showed no change in the number of sleep spindles.

Clicking noises delivered to subjects at the same time as the subjects undergo the sleep spindles of stage II sleep and as the subjects ascend from slow wave sleep towards REM sleep have been shown to increase central nervous system excitability.

Transcranial magnetic stimulation (TMS) refers to a non-invasive excitation of neurons in the brain by utilizing magnetic fields to induce electric currents the brain. An example of TMS may involve placing a treatment coil that generates a magnetic field near a subject's head. The magnetic field may induce an electrical current in the brain causing neurons to fire, which may induce various chemical changes in the brain.

SUMMARY OF THE INVENTION

In one aspect, the present invention provides a method of stimulating a subject's brain. The method may include providing stimulation apparatus (e.g., TMS apparatus, auditory stimulation apparatus, visual stimulation apparatus, olfactory stimulation apparatus, somatosensory stimulation apparatus, etc.) for delivering stimulation to a subject and monitoring apparatus (e.g., EEG apparatus, EOG apparatus, EMG apparatus, etc.) to measure the state of the subject, e.g., through the activity of the subject's brain. The method may further include positioning the stimulation apparatus where the subject can receive the stimulation, delivering stimulation from the stimulation apparatus to the subject during one or more first periods when the subject is awake, and delivering stimulation from the stimulation apparatus to the subject during one or more second periods when the subject is asleep.

In another aspect, the present invention provides a stimulation system for stimulating a subject. The system may include a learning component and a consolidation component. The learning component may include auditory stimulation apparatus for delivering one or more selected auditory stimulations to the subject and one or more self-actuation inputs operably coupled to the auditory stimulation apparatus for self-actuation by the subject to deliver at least one selected auditory stimulation of the one or more selected auditory stimulations to the subject. The consolidation component may include monitoring apparatus for monitoring the sleep state of a subject, wherein the monitoring apparatus comprises one or more electrodes, auditory stimulation apparatus for delivering one or more selected auditory stimulations to the subject, and a controller electrically coupled to the monitoring apparatus to receive input regarding the sleep state of the subject from the monitoring apparatus and the auditory stimulation apparatus to operate the auditory stimulation apparatus. The controller may utilize the input from the monitoring apparatus to determine when the subject is in one or more selected sleep states. Further, the controller may operate the auditory stimulation apparatus to deliver at least one selected auditory stimulation of the one or more selected auditory stimulations previously delivered by the learning component to the subject during at least one selected sleep state of the one or more selected sleep states.

In another aspect, the present invention provides a method of stimulating a subject's brain. The method may include providing stimulation apparatus for delivering stimulation to a subject and electroencephalography apparatus to measure the electrical activity of the subject's brain. The method may further include positioning the stimulation apparatus where the subject can receive the stimulation, delivering stimulation from the stimulation apparatus to the subject during one or more first periods when the subject is awake, and delivering stimulation from the stimulation apparatus to the subject during one or more second periods when the subject is asleep.

In another aspect, the present invention provides a method of stimulating a subject's brain. The method may include providing stimulation apparatus for delivering transcranial magnetic stimulation and electroencephalography apparatus to measure the electrical activity of the subject's brain. The method may further include positioning the stimulation apparatus proximate the subject's brain, wherein the stimulation apparatus is located external to the subject's skull, delivering transcranial magnetic stimulation from the stimulation apparatus to the subject's brain during a first period when the subject is awake, and delivering transcranial magnetic stimulation from the stimulation apparatus to the subject's brain during a second period when the subject is asleep.

In another aspect, the present invention provides a method of stimulating a subject's brain. The method may include providing auditory stimulation apparatus for delivering auditory stimulation to a subject and electroencephalography apparatus to measure the electrical activity of the subject's brain. The method may further include positioning the auditory stimulation apparatus where the subject can hear the auditory stimulation, delivering auditory stimulation from the auditory stimulation apparatus to the subject during one or more first periods when the subject is awake, and delivering auditory stimulation from the auditory stimulation apparatus to the subject during one or more second periods when the subject is asleep.

In another aspect, the present invention provides a stimulation system. The stimulation system may include electroencephalography apparatus, stimulation apparatus, and a controller electrically coupled to the electroencephalography apparatus and the stimulation apparatus. The electroencephalography apparatus may includes one or more electrodes. The controller may receive input from the electroencephalography apparatus, and the controller may control the stimulation apparatus.

In another aspect, the present invention provides a stimulation system. The stimulation system may include electroencephalography apparatus, transcranial magnetic stimulation apparatus, and a controller electrically coupled to the electroencephalography apparatus and the transcranial magnetic stimulation apparatus. The electroencephalography apparatus may include one or more electrodes. The transcranial magnetic stimulation apparatus may include one or more treatment coils. The controller may receive input from the electroencephalography apparatus, and the controller may control the transcranial magnetic stimulation apparatus.

In another aspect, the present invention provides a stimulation system. The stimulation system may include electroencephalography apparatus, auditory stimulation apparatus, and a controller electrically coupled to the electroencephalography apparatus and the auditory stimulation apparatus. The electroencephalography apparatus may include one or more electrodes. The controller may receive input from the electroencephalography apparatus, and the controller may control the auditory stimulation apparatus.

In still another aspect, the present invention provides a stimulation system. The stimulation system may include monitoring apparatus for monitoring the sleep state of a subject, auditory stimulation apparatus for delivering one or more selected auditory stimulations to the subject one or more self-actuation inputs for self-actuation by the subject to deliver at least one selected auditory stimulation of the one or more selected auditory stimulations to the subject, and a controller electrically coupled to the monitoring apparatus, the auditory stimulation apparatus, and the one or more self-actuation inputs. The monitoring apparatus may include one or more electrodes. Further, the controller may receive input from the monitoring apparatus to determine if the subject is in one or more the selected sleep states. Still further, the controller may operate the auditory stimulation apparatus to deliver at least one of the one or more selected auditory stimulations to the subject when the subject is determined to be in one or more of the selected sleep states.

In yet still another aspect, the present invention provides a method of stimulating a subject's brain. The method may include providing auditory stimulation apparatus for delivering one or more auditory stimulations to a subject and providing monitoring apparatus to monitor the state of the subject. Further, the method may include positioning the auditory stimulation apparatus where the subject can hear the auditory stimulation and delivering at least one auditory stimulation of the one or more auditory stimulations from the auditory stimulation apparatus to the subject during one or more first periods when the subject is awake. Still further, the method may include delivering the at least one auditory stimulation of the one or more auditory stimulations from the auditory stimulation apparatus to the subject during one or more second periods when the subject is asleep.

The above summary is not intended to describe each embodiment or every implementation of the present invention. Rather, a more complete understanding of the invention will become apparent and appreciated by reference to the following Detailed Description of Exemplary Embodiments and claims in view of the accompanying figures of the drawing.

BRIEF DESCRIPTION OF THE DRAWING

FIG. 15 is a diagrammatic representation of one exemplary embodiment of a stimulation system according to the present invention.

DESCRIPTION OF EXEMPLARY EMBODIMENTS

Figure 1:
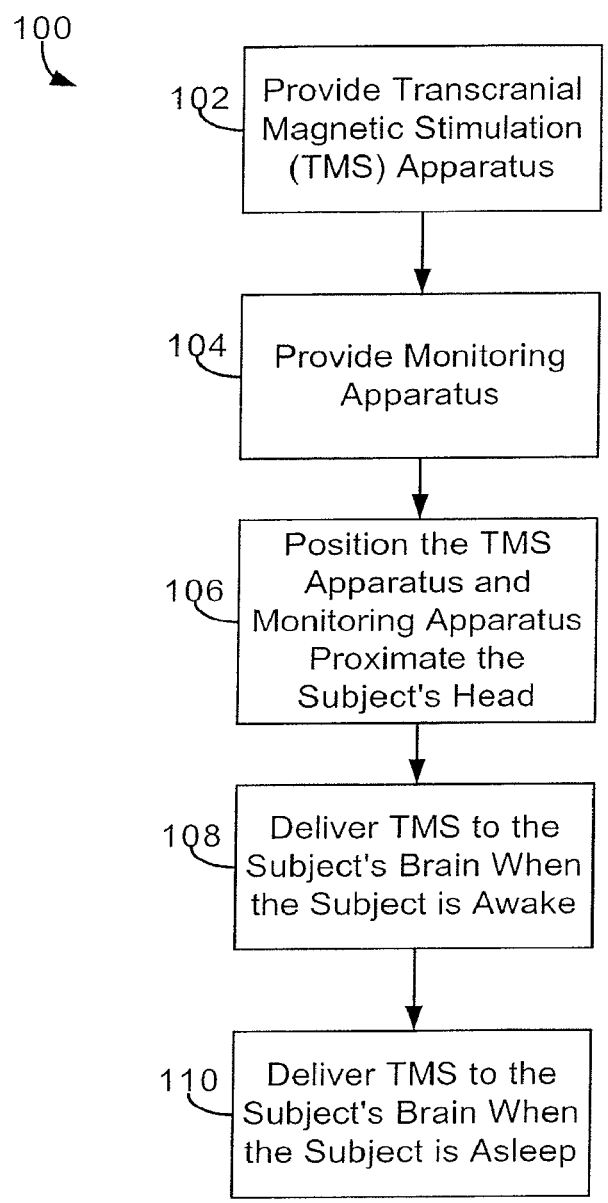
FIG. 1 is a flow chart of one exemplary method of stimulating a subject's brain according to the present invention.

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

As used herein, "a," "an," "the," "at least one," and "one or more" are used interchangeably. The term "and/or" (if used) means one or all of the listed elements or a combination of any two or more of the listed elements.

FIG. 1 depicts one exemplary method 100 of stimulating a subject's brain according to the present invention. In this method, TMS apparatus may be provided 102. The TMS apparatus used in this method 100 may be any apparatus capable of providing TMS to a subject. Examples of some potentially suitable TMS apparatus may include, e.g., a NeuroStar TMS Therapy System from Neuronetics, Inc. The TMS apparatus may include a power supply, a control system, a display system, at least one treatment coil, and/or any other component as would be known by one of ordinary skill in the art. The TMS apparatus may be autonomous, or may be operated by an operator. In at least one embodiment, the subject may self-administer the TMS. The TMS apparatus may be stationary or portable (in which case it may include a portable power supply).

Monitoring apparatus 104 may also be provided in connection with the systems of the present invention. The monitoring apparatus may include a power supply, a control system, a display system, at least one electrode, and/or any other component as would be known by one of ordinary skill in the art. The monitoring apparatus may be autonomous, or may be operated by an operator. In at least one embodiment, the subject may self-administer the monitoring apparatus. The monitoring apparatus may be stationary or portable (in which case it may include a portable power supply).

The TMS apparatus and the monitoring apparatus may be positioned proximate the subject's brain 106. As described herein, the TMS apparatus may include one or more treatment coils that may provide magnetic stimulation to, e.g., the subject's brain by producing one or more magnetic fields. The treatment coils may be positioned proximate one or more selected portions of the subject's brain. Further, as described herein, the monitoring apparatus may include one or more electrodes to detect electrical activity (e.g., EEG) of the subject's brain, muscular activity (e.g., EMG) of the subject, and/or ocular activity (e.g., EOG) of the subject. The one or more electrodes may be positioned proximate one or more portions of the subject's head and/or subject's brain. In at least one embodiment according to the present invention, the TMS apparatus and the monitoring apparatus may be integrated so that, e.g., the same apparatus may be positioned proximate the subject's head and provide both the TMS and monitoring functions.

The treatment coils of the TMS apparatus may be positioned proximate the subject's brain to stimulate one or more selected portions of the subject's brain. For example, the treatment coils may be positioned to stimulate the various cortical and deep brain structures including the frontal lobes, the temporal lobes, the parietal lobes, the occipital cortex, the hippocampus, the amygdala, etc. The selected portions of the brain stimulated by TMS may be selected to correspond to the learning task that the method is intended to improve as understood by one of ordinary skill in neurophysiology. For example, a subject's precentral gyrus corresponding to the right hand may be stimulated with TMS in an attempt to improve the subject's coordination of a learned skill involving the right hand because the precentral gyrus corresponding to the right hand is known in neurophysiology to correspond with right hand movements.

The electrodes of the monitoring apparatus may be positioned proximate the subject's head to monitor, e.g., one or more selected portions of the subject's brain and/or head, etc. For example, the electrodes may be positioned proximate the subject's eyes, forehead, frontal lobes, temporal lobes, parietal lobes, occipital lobes, the cerebral cortex overlaying the hippocampus, amygdala, etc. The one or more selected portions of the subject's brain and/or head to be monitored by the monitoring apparatus may be selected based on what portions of the brain may be involved in the task at hand. Additionally, the monitoring apparatus may monitor the state of consciousness or sleep stage the subject is in at any given moment. For example, a subject's frontal lobe just above the eye may be monitored by the monitoring apparatus because the stage of sleep may be determined through an analysis of brain waves (e.g., EEG), eye movements (e.g., EOG), and muscle tone (e.g., EMG).

The TMS as delivered to a subject may include magnetic fields oscillating at one or more selected frequency ranges, e.g., a frequency of about 3 hertz or more, about 8 hertz or less, or faster or slower frequency ranges. Other variations in the delivery of TMS may include variations in magnetic field strength. For example, the magnetic field strength used in connection with the present invention as measures at the subject's scalp may be about 1 tesla or more, about 4 teslas or less, etc. Further, other variations in the delivery of TMS may include variations in waveform morphology and/or variations in the patterns of waveforms through time.

Although the method 100 depicted in FIG. 1 involves positioning both the TMS apparatus and the monitoring apparatus proximate the subject's head before delivering TMS to the subject's brain when the subject is awake 108, other embodiments may not position the monitoring apparatus proximate the subject's head until after the TMS is delivered when the subject is awake 108 (i.e., before TMS is delivered when the subject is asleep 110). In other words, the monitoring apparatus may not be used while the subject is awake.

The TMS may be delivered to the subject when the subject is awake during a selected time period, during one or more selected time periods, or continuously. The delivery of TMS to the subject's brain 110 while the subject is awake may only occur while the subject is learning a specific task. Such learning may include memorization, reading and comprehension, motor skills, verbal fluency, any other learning paradigm, etc. Further, the delivery of TMS to the subject's brain 110 while the subject is awake may only occur when the electrical activity in the subject's brain indicates that the subject is in a particular state. For example, as described herein, one such state may be when a subject's hippocampal brainwaves are operating in the theta frequency (or any other selected frequency range).

The TMS may be delivered to the subject when the subject is asleep during a selected time period, during one or more selected time periods, or continuously. The delivery of TMS while a subject is both awake and asleep may create an association between the learning task and/or tasks that the subject experienced during the awake period and the memory consolidation of such learning task or tasks while sleeping.

Figure 2:
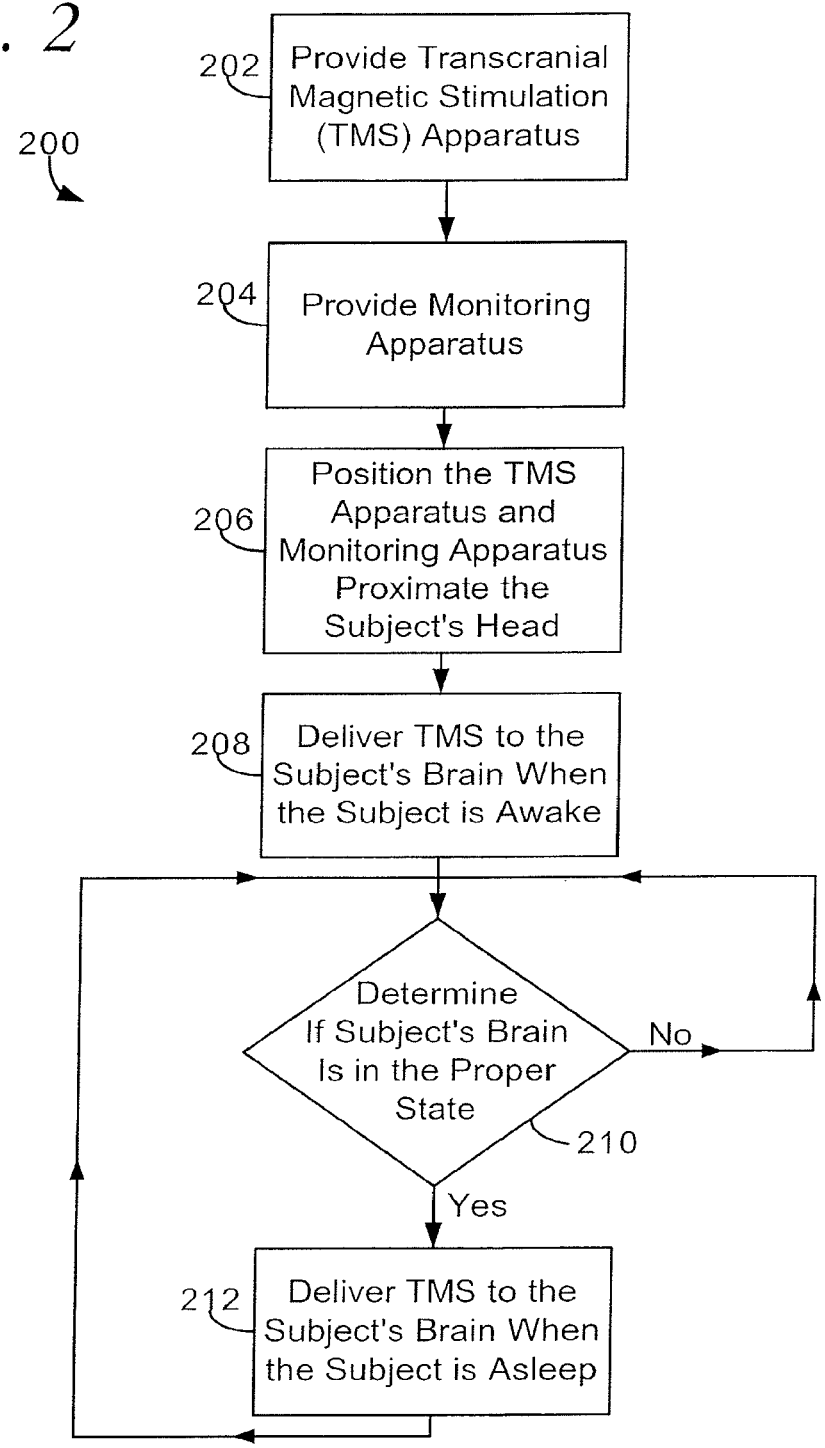
FIG. 2 is a flow chart of another exemplary method stimulating subject's brain according to the present invention.

FIG. 2 depicts another exemplary method of stimulating a subject's brain according to the present invention. The steps 202, 204, 206, 208, and 212 are similar to the steps 102, 104, 106, 108, and 110, respectively, described herein with respect to FIG. 1. The method 200 depicted in FIG. 2 includes determining if the subject's brain is in a selected state before delivering TMS to the subject's brain. This selective delivery of TMS may be performed during selected sleep stages and/or selected portions of stages of the subject's sleep cycle as described herein.

The determination step 210 of method 200 may, for example, include determining if the subject is experiencing actual rapid eye movement (e.g., using the monitoring apparatus), and if so, delivering a period of TMS 212. After the delivery of TMS 212, the method 200 may loop back to determine if the subject's brain is in a selected state 210 before again delivering TMS. For example, the method may include waiting for the subject to experience actual rapid eye movement before delivering another period of TMS.

The TMS may be delivered for a fixed time period (e.g., a fraction of a second). Alternatively, the period of time over which TMS is delivered may vary. For example, the period of time over which TMS is delivered may be based upon real time feedback from the monitoring apparatus. The monitoring apparatus may detect the various frequencies or sleep characteristics that may trigger the method 200 to initiate and/or maintain the TMS delivery step 212 or to terminate TMS delivery and return to the determination mode 210. The method 200 may continuously loop or may only loop a selected number of times. In at least one embodiment, the number of loops the method 200 may undergo may be based on the hours of sleep per night a subject generally sleeps, is expected to sleep, etc.

TMS may be delivered 212 to the subject during a selected time period when the subject is asleep and the electrical activity of the subject's brain is, for example, determined 210 to be undergoing sawtooth waveforms before rapid eye movement. TMS may alternatively or also be delivered during other physical and/or neurophysiological activity. For instance, TMS may be delivered to the subject when the subject is determined to be undergoing slow wave sleep (in addition to or in place of, e.g., delivery during sawtooth wave activity).

Further, TMS may be delivered 212 to the subject during sleep when the subject is determined 210 to be undergoing a more specific portion of the sleep cycle. For example, TMS may be delivered to a subject when the subject is undergoing sleep spindles. In such a case, the TMS may be delivered for a pre-selected fixed time period that is long enough to, e.g., deliver TMS during an entire typical sleep spindle episode. Alternatively, the period of time over which TMS is delivered may vary. For example, the period of time over which TMS is delivered may be based on feedback, with the TMS delivery terminating when the sleep spindle episode is over. In another example, TMS may be delivered to a subject during sleep spindles specifically when the subject is undergoing the short period of stage II sleep immediately preceding rapid eye movement sleep. Again, this short section of the sleep cycle may be determined by real time feedback from monitoring apparatus.

Further, for example, TMS may be delivered to a sleeping subject when selected brain wave frequencies are detected. Such selected brain waves frequencies may correspond to various memory consolidation functions of the brain. For instance, TMS may be delivered to the subject based on electrical activity of one or more selected portions of the subject's brain, e.g., when the selected portion(s) of the subject's brain is/are oscillating at a frequency of about 3 hertz to about 8 hertz (the theta frequency). As described herein, the theta frequency has been seen in awake subjects while they are learning, and again, when the subjects are asleep.

In other embodiments, TMS may be delivered when selected portion(s) of a subject's brain is/are oscillating within any other selected frequency range. For example, TMS may be delivered when the electrical activity of the selected portion(s) of the subject's brain is/are oscillating at about 26 hertz to about 70 hertz (i.e., faster frequencies observed during REM sleep), about 0.5 hertz to about 3 hertz (i.e., frequencies observed during slow wave sleep), about 12 hertz to about 14 hertz (i.e., frequencies observed during sleep spindle periods), etc.

Further, the TMS may be delivered to a sleeping subject's brain during various physical phenomena. For instance, TMS may be delivered to the subject when the subject undergoes actual rapid eye movements (e.g., monitored using EMG and/or EOG apparatus of the monitoring apparatus). In at least one embodiment, such determination is based upon on the actual eye movements, and as such, delivery of TMS may stop upon termination of the rapid eye movements. Alternatively, the TMS may be delivered for a pre-selected fixed period of time that may, e.g., be based on the duration of a typical period of rapid eye movement.

In at least another embodiment, the determination step 210 of method 200 may include determining when the electrical activity in the subject's brain is indicative of an increase in slope of the 1-2 hertz slow wave waveform of the electrical activity of slow wave sleep or when the electrical activity in the subject's brain is indicative of an impending increase in slope of the waveform of the electrical activity.

The determination step 210 of method 200 may include determining the existence of two or more conditions, which conditions may be dependent or independent from each other. For example, the method 200 may include determining if the subject's brain waves are undergoing sawtooth waveforms before bursts of rapid eye movement or undergoing sleep spindles before delivering a period of TMS 212.

Determining if a subject's brain is in the proper state 210 (e.g., the occurrence of sawtooth waves and/or phasic eye movements during REM sleep) may be accomplished utilizing monitoring apparatus positioned proximal to the subject's eye, forehead, temporalis muscle, over the frontal lobe, over the temporal lobe, over the parietal lobe, over occipital lobe, etc.

Figure 3:
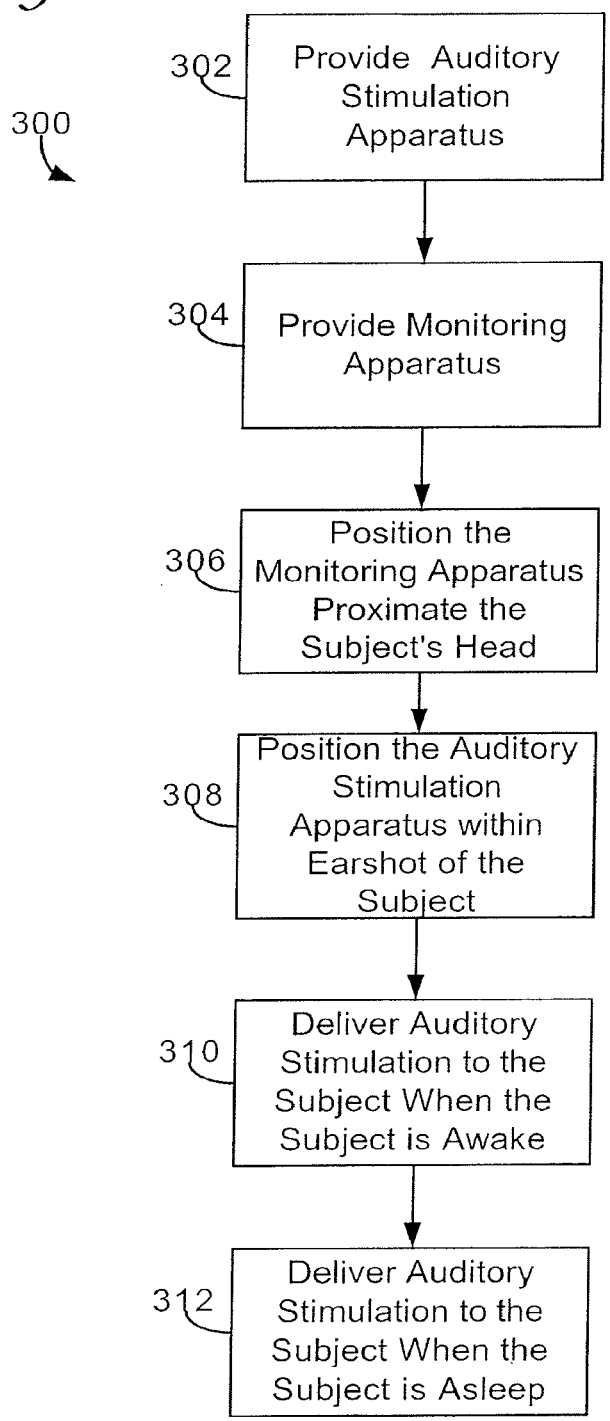
FIG. 3 is a flow chart of another exemplary method stimulating subject's brain according to the present invention.

FIG. 3 depicts another exemplary method 300 of providing stimulation according to the present invention. In this method, auditory stimulus may be delivered to the subject during an awake period and during an asleep period. The delivery of auditory stimulation when a subject is awake and then after the subject falls asleep may create an association between learning tasks the subject experienced during the awake period and the memory consolidation of such learning tasks during the asleep period.

In this method, auditory stimulation apparatus may be provided 302. Auditory stimulation apparatus may include, e.g., a power supply, a control system, a display system, headphones, speakers, tapes, compact discs, memory, and/or any other component as would be known by one of ordinary skill in the art. The auditory stimulation apparatus may work in conjunction with a portable audio device like, e.g., an Apple iPod, a MP3 player, a compact disc (CD) player, etc. Further, the auditory stimulation apparatus may be a non-portable audio device like, e.g., a home stereo system, radio, etc.

A subject may configure the auditory stimulation apparatus to deliver different types of auditory stimulation to, e.g., correspond to different types of awake learning tasks. For example, a subject may configure the auditory stimulation apparatus to deliver a first type of auditory stimulation, such as, e.g., classical music (or classical music of a specific composer), while the subject is learning a selected type of material (e.g., math, grammar, history, etc.). Further, for example, a subject may configure the auditory stimulation apparatus to deliver a second type of auditory stimulation, such as, e.g., ambient "water flowing" sounds, while the subject is learning vocabulary. Still further, for example, a subject may configure the auditory stimulation apparatus to deliver a third type of auditory stimulation, such as, e.g., short auditory tones (e.g., about 1 kilohertz ore more, 2 kilohertz or less, etc. for about one-half second or less, about 1 second or more, about 1 second or less, etc.), that are selected to correspond to a selected learning activity.

More specifically, a subject may further configure the auditory stimulation apparatus to deliver different auditory stimulation for each sub-task of the learning task. For example, a subject may configure the auditory stimulation apparatus to deliver a different short snippet (e.g., 5 seconds or less) of classical music for each math problem while the subject is learning math. A subject may apply these configurations described herein to the auditory stimulation apparatus, the stimulation system, and/or to a configuration apparatus that configures the auditory stimulation apparatus and/or stimulation system.

Further, different learning tasks or sub-tasks may be preferred to be stimulated during different periods of sleep. As such, auditory stimulations corresponding to specific learning tasks and/or sub-tasks may only be delivered during specific periods of sleep (e.g., the auditory stimulations corresponding to motor tasks may be delivered when the subject is undergoing stage II sleep, or auditory stimulations corresponding to non-motor tasks may be delivered when the subject is undergoing sleep spindles).

Still further, the stimulation system may include one or more self-actuation inputs such that a user may self-actuate different auditory stimulations (or visual, olfactory, somatosensory, or transcranial magnetic stimulations) while learning. A subject utilizing the self-actuation inputs may be able to self-actuate each of the auditory stimulations such that every learning task or sub-task may have the same or a different auditory stimulation. The self-actuated stimulations may be recorded by the stimulation system such that the selected stimulations may be re-delivered to the subject during, e.g., the asleep period, specific stages of sleep, different states of the subject, etc.

Monitoring apparatus 304 may also be provided in connection with the systems of the present invention. The monitoring apparatus may be the same as or similar to the monitoring apparatus as described with reference to step 104 of the method 100 depicted in FIG. 1. Further, the monitoring apparatus may be positioned proximate the subject's head 306 in substantially the same way as described with reference to step 106 of method 100 of FIG. 1. In at least one embodiment, the auditory stimulation apparatus and the monitoring apparatus may be integrated in a single unit. In at least another embodiment, the auditory stimulation apparatus and/or the monitoring apparatus may be an add-on, or plug-in, to an existing audio system, e.g., a portable music device. Further, in at least one embodiment, the auditory stimulation apparatus and the monitoring apparatus may be integrated into a removable adhesive patch.

The auditory stimulation apparatus may be positioned within earshot of the subject 308 so that the subject may hear the auditory stimulation both during the awake period and asleep period. Although the same auditory stimulation apparatus may be used for both the awake period and the asleep period, different auditory stimulation apparatus may be used during each period. For example, a subject may use a portable audio device during the awake period and may use a larger or less portable audio device, e.g., a home stereo, during the asleep period.

Although the method 300 depicted in FIG. 3 may involve positioning both the auditory stimulation apparatus and the monitoring apparatus proximate the subject's head before delivering auditory stimulation when the subject is awake, other embodiments may not position the monitoring apparatus proximate the subject's head until after the auditory stimulation is delivered when the subject is awake (i.e., before auditory stimulation is delivered when the subject is asleep). In other words, the monitoring apparatus may not be positioned and/or used while the subject is awake.

The method may further include delivering auditory stimulation to an awake subject during a learning period. In at least one embodiment, an example of such auditory stimulation may be short auditory snippets, e.g., various unique cell phone ring tones lasting several seconds in duration, portions of songs, combinations of notes and/or frequencies, etc.

The auditory stimulation may be delivered to the subject when the subject is awake during a selected time period, during one or more selected time periods, or continuously. The delivery of auditory stimulation while the subject is awake may only occur while the subject is learning a specific task. Such learning may include memorization, reading and comprehension, motor skills, verbal fluency, any other learning paradigm, etc.

Further, the auditory stimulation may be delivered only when the subject is in the proper state which, e.g., may be determined by the electrical activity in the subject's brain that indicates that the subject is in a particular state. For example, as described herein, one such state may be when a subject's brainwaves are operating in the theta frequency (or any other selected frequency range).

The auditory stimulation may be delivered to the subject when the subject is asleep during a selected time period, during one or more selected time periods, or continuously. The delivery of auditory stimulation while a subject is both awake and asleep may create an association between the learning task or tasks that the subject experienced during the awake period and the memory consolidation of such learning task or tasks during sleep.

For example, the method may include delivering auditory stimulation to the subject when the subject is asleep during a memory consolidation period 312. In this step, the same auditory stimulation that was delivered to the subject while awake during the learning period may be delivered to the subject while asleep during the memory consolidation period. During the asleep period, the volume of the auditory stimulation may be adjusted as to not reach a level that may awaken the subject (which level may vary among subjects).

Figure 4:
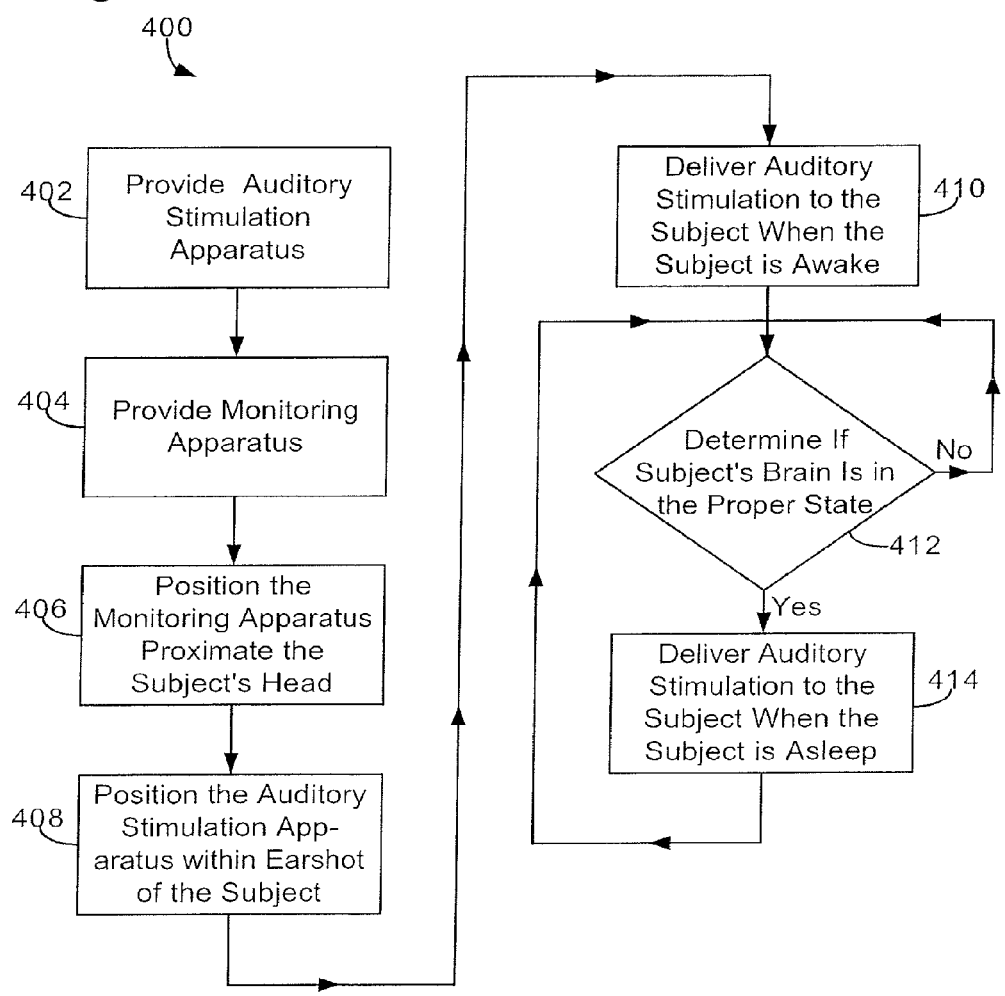
FIG. 4 is a flow chart of another exemplary method stimulating subject's brain according to the present invention.

FIG. 4 depicts another exemplary method of providing stimulation according to the present invention. The steps 402, 404, 406, 408, 410 and 414 are similar to the steps 302, 304, 306, 308, 310, and 312 respectively, described herein with respect to FIG. 3.

The method depicted in FIG. 4, however, includes determining if the subject is in a selected state before delivering auditory stimulation to the subject when the subject is asleep 412. This step may allow auditory stimulation to be delivered at selected stages, or selected portions of stages of the subject's sleep cycle as described herein. Step 412 may be substantially the same as step 210 of method 200 of FIG. 2 except the determination may be made before delivering auditory stimulation instead of TMS as described in method 200. Further, different auditory stimulation corresponding to different learning tasks may be delivered during while the subject is certain states, during or portions of stages of the subject's sleep cycle. For example, the auditory stimulation corresponding to a selected learning task or tasks (e.g., math, grammar, etc.) may be delivered while a subject's electrical activity indicates sawtooth waves of REM sleep. Further, for example, the auditory stimulation corresponding to motor skill tasks may be delivered while a subject is undergoing sleep spindles in stage II sleep.

The determination step 412 of method 400 may, for example, include determining if the subject is experiencing actual rapid eye movement (e.g., utilizing EMG and/or EOG apparatus of the monitoring apparatus), and if so, delivering a period of selected auditory stimulation 414. After the delivery of auditory stimulation 414, the method 400 may loop back to determine if the subject is in a selected state 412 before again delivering auditory stimulation. For example, the method may include waiting for the subject to experience actual rapid eye movement before delivering another period of auditory stimulation.

The auditory stimulation may be delivered for a fixed time period (e.g., several seconds). Alternatively, the period of time over which auditory stimulation is delivered may vary. For example, the period of time over which auditory stimulation is delivered may be based upon real time feedback from the monitoring apparatus (e.g., EEG apparatus, EMG apparatus, EOG apparatus, etc.). The monitoring apparatus may detect the various frequencies or sleep characteristics that may trigger the method 400 to initiate and/or maintain the auditory stimulation delivery 414 or to terminate auditory stimulation delivery and return to the determination mode 412. The method 400 may continuously loop or may only loop a selected number of times. In at least one embodiment, the number of loops the method 400 may undergo may be based on the hours of sleep per night a subject generally sleeps, is expected to sleep, etc.

For example, the monitoring apparatus may include EEG apparatus that may continuously sample the neural activity of the subject at any suitable frequency, e.g., about 140 hertz or less, about 100 hertz or less, etc. to monitor the neural activity of the subject that oscillates at about 0.5 hertz or more, about 2 hertz or more, about 70 hertz or less, about 90 hertz or less, etc. In at least one embodiment, the EEG apparatus of the monitoring apparatus may monitor neural activity of the subject that oscillates between about 0.5 hertz to about 70 hertz. Further, the rate at which the EEG apparatus of the monitoring apparatus may sample the neural activity of the subject may be selectable by, e.g., a switch or an administrator prior to attaching the stimulation patch to the subject.

Further, EEG apparatus of the monitoring apparatus may acquire and/or store data relating to the neural activity of the subject at selected intervals, e.g., 1 minute of every 5 minutes, 15 seconds of every 1 minute, etc. The selected interval during which data is stored may be chosen in view of the amount of data capable of being stored within the system.

The systems and methods described herein may monitor the neural, muscular, and/or ocular activity of the subject for a selected period of time. As used herein, "monitor" or "monitoring" may be defined as any activity that includes acquiring signal activity. As such, "monitor" or "monitoring" may include recording signal activity, analyzing signal activity, numerically transforming signal activity, providing feedback in response to signal activity, etc.

Auditory stimulation may be delivered to the subject during a selected time period when the subject is asleep and the electrical activity of the subject's brain is, for example, determined 414 to be undergoing sawtooth waveforms before rapid eye movement. Auditory stimulation may alternatively or also be delivered during other physical and/or neurophysiological activity. For instance, auditory stimulation may be delivered to the subject when the subject is determined to be undergoing slow wave sleep (in addition to or in place of, e.g., delivery during sawtooth wave activity).

Further, delivery of auditory stimulation 414 to the subject during sleep may occur when the subject is determined 412 to be undergoing a more specific portion of the sleep cycle. For example, auditory stimulation may be delivered to a subject when the subject is undergoing sleep spindles. In such a case, the auditory stimulation may be delivered for a pre-selected fixed time period that is long enough to, e.g., deliver auditory stimulation during an entire typical sleep spindle episode. Alternatively, the period of time over which auditory stimulation is delivered may vary. For example, the period of time over which auditory stimulation is delivered may be based on feedback, with the auditory stimulation delivery terminating when the sleep spindle episode is over. In another example, auditory stimulation may be delivered to a subject during sleep spindles when the subject is undergoing the short period of stage II sleep immediately preceding rapid eye movement sleep. Again, this short section of the sleep cycle may be determined by real time feedback from the monitoring apparatus.

Further, for example, auditory stimulation may be delivered to a sleeping subject when selected brain wave frequencies are detected. Such selected brain wave frequencies may correspond to various memory consolidation functions of the brain. For instance, auditory stimulation may be delivered to the subject based on electrical activity of one or more selected portions of the subject's brain, e.g., when the selected portion(s) of the subject's brain is/are oscillating at a frequency of about 3 hertz to about 8 hertz (the theta frequency). As described herein, the theta frequency has been seen in awake subjects while they are learning and, again, when the subjects are asleep.

In other embodiments, auditory stimulation may be delivered when selected portion(s) of a subject's brain is/are oscillating within any other selected frequency range. For example, auditory stimulation may be delivered when the electrical activity of the selected portion(s) of the subject's brain is/are oscillating at about 26 hertz to about 70 hertz (i.e., the faster frequencies observed during REM sleep), about 0.5 hertz to about 3 hertz (i.e., frequencies observed during slow wave sleep), about 12 hertz to about 14 hertz (i.e., frequencies observed during sleep spindle periods), etc.

Further, the auditory stimulation may be delivered to a sleeping subject's brain during various physical phenomena.

For instance, auditory stimulation may be delivered to the subject when the subject undergoes during actual rapid eye movements (e.g., as detected by the monitoring apparatus). In at least one embodiment, such determination is based upon on the actual eye movements, and as such, delivery of auditory stimulation may stop upon termination of the rapid eye movements. Alternatively, the auditory stimulation may be delivered for a pre-selected fixed period of time that may, e.g., be based on the duration of a typical period of rapid eye movement.

In at least another embodiment, the determination step 412 of method 400 may include determining when the electrical activity in the subject's brain is indicative of an increase in slope, is undergoing 1-2 hertz slow wave waveforms indicative of slow wave sleep, etc.

The determination step 412 of method 400 may include determining the existence of two or more conditions. The two or more conditions may be dependent or independent from each other. Determining if a subject is in a selected state 412 (e.g., the occurrence of sawtooth waves and/or phasic eye movements during REM sleep) may be accomplished utilizing monitoring apparatus positioned proximal to the subject's eye, forehead, temporalis muscle, over the frontal lobe, over the temporal lobe, over the parietal lobe, over the occipital lobe, etc.

The determination step 412 of method 400 may include determining the existence of two or more conditions, which may be dependent on each other or independent from each other. For example, the method 400 may include determining the existence of two independent conditions such as sawtooth waveforms (before rapid eye movement) and sleep spindles, with the existence of the two independent conditions triggering a period of auditory stimulation 414. In such an embodiment, the auditory stimulation 414 could be initially triggered by either sawtooth waveforms or undergoing sleep spindles. In another example, the method 400 may include determining the existence of two independent conditions such as actual rapid eye movement or slow wave sleep.

In another example, the method 400 may include determining the existence of two dependent conditions such as sawtooth waveforms and the subsequent rapid eye movement and having the existence of the two dependent conditions triggering a period of auditory stimulation. In such an embodiment, the auditory stimulation 414 may be triggered by sawtooth waveforms before rapid eye movements of rapid eye movement sleep.

Such two or more condition determination steps may include any or all of the conditions described herein relating to neurophysiological information, physical phenomena, etc.

Although the two or more independent/dependent condition determination steps are discussed in reference to step 412 of method 400 depicted in FIG. 4, such two or more condition determination steps may be utilized with any other method described herein (e.g., the transcranial magnetic stimulation method 200 depicted in FIG. 2).

Figure 5A:
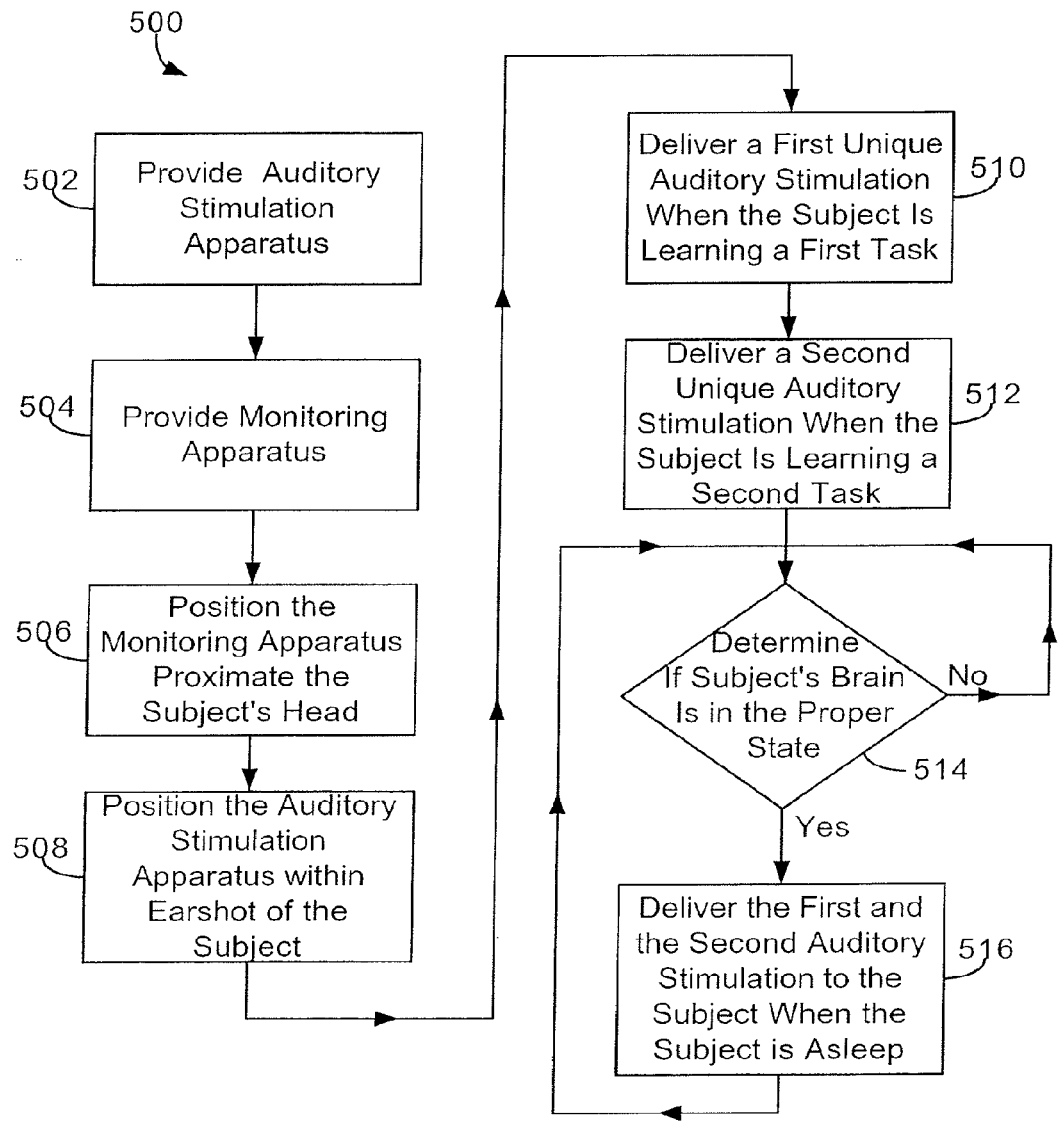
FIG. 5A is a flow chart of another exemplary method stimulating subject's brain according to the present invention.

FIG. 5A depicts another exemplary method of providing stimulation according to the present invention. The steps 502, 504, 506, and 508, are similar to the steps 302, 304, 306, and 308, respectively, described herein with respect to FIG. 3. Step 514 is similar to step 210 described herein with respect to FIG. 2.

The method 500 depicted in FIG. 5A, however, includes delivering a first unique auditory stimulation to the subject when the subject is learning a first task 510 and delivering a second unique auditory stimulation to the subject when the subject is learning a second task 512. The different auditory stimulation may be in the form of, e.g., various unique cell phone ring tones lasting several seconds in duration, portions of songs, combinations of notes and/or frequencies, etc. The delivery of the first and the second unique auditory stimulation for the different learning tasks during the awake period and the asleep period may create an association between the different learning tasks and the memory consolidation of each learning task during an asleep period.

In at least one embodiment, a specific auditory stimulation may be chosen to be played/delivered while learning a specific task, procedure, fact, relationship, etc. A different auditory stimulation may be used for each specific thing to be learned, but the same auditory stimulation may be used if the same information is rehearsed more than once, so that a selected auditory stimulation may be specific to each task, procedure, fact, relationship, etc. The auditory stimulation may not only occur during learning but should also occur during sleep, for example, during the sleep spindles of stage II sleep (preferably, but not necessarily, during the stage II sleep seen following slow wave sleep just prior to the onset of REM sleep).

In at least another embodiment, a different auditory stimulation may be delivered/played to the subject for each particular task. For example, a first auditory stimulation may be delivered to the subject during vocabulary memorization while a second auditory stimulation may be delivered to the subject during fine motor tasks. Further, each particular task could be further defined. For example, a different auditory stimulation may be delivered to the subject for each different word during vocabulary memorization, or for each different type of word during vocabulary memorization (e.g., verbs, nouns, adjectives, etc.), or for different types of facts, e.g., dates in history with corresponding events, or other such information that may be learned and remembered.

Figure 5B:
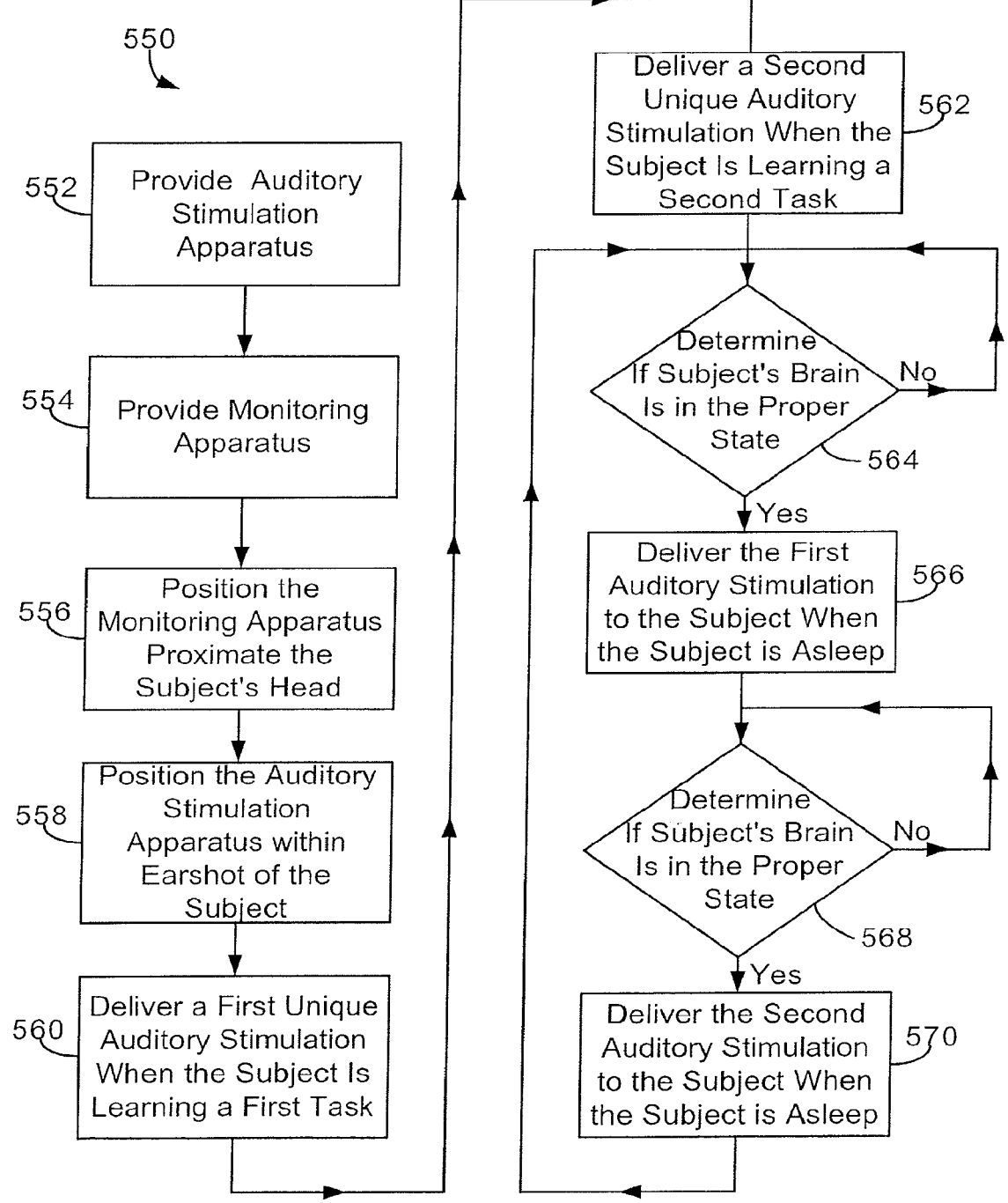
FIG. 5B is a flow chart of still another exemplary method stimulating subject's brain according to the present invention.

FIG. 5B depicts still another exemplary method of providing stimulation according to the present invention. The steps 552, 554, 556, 558, 560, 562, and 568/568 are similar to the steps 502, 504, 506, 508, 510, 512, and 514 respectively, described herein with respect to FIG. 5.

The method 550 depicted in FIG. 5B, however, includes two determination steps 564, 568. The first determination step 564 may determine if the subject's brain is in the proper state for delivering of auditory stimulation corresponding to the first learning task. For example, step 564 may be monitoring the brain of the subject for sleep spindles and upon detecting sleep spindles, the step 564 may release to step 566 to deliver the one or more auditory stimulations corresponding to the first learning task, e.g., a motor skill task. The second determination step 568 may monitor the subject for a different state corresponding to a different auditory stimulation for a second learning task. For example, step 568 may be monitoring the subject for rapid eye movement and upon detecting rapid eye movement, the step 568 may release to step 570 to deliver the second auditory stimulation, different from the first auditory stimulation, that corresponds to the second learning task, e.g., visual learning task.

Although as depicted in FIG. 5B, the monitoring apparatus may only be monitoring for the first state to trigger the delivery of the first auditory stimulation before monitoring for the second state to trigger the delivery of the second auditory stimulation, in other embodiments, the monitoring apparatus may monitor for all states simultaneously such that it can deliver the corresponding auditory stimulation for each state when the subject undergoes such state. For example, a single determination step may exist for detecting a first state and a second state. Regardless of the detection of the first state, if the second state is detected, the second stimulation may be delivered.

Although the steps in the methods depicted in FIGS. 1-5 are listed and/or described in a specific order, the sequences of steps may different than described herein as would be known by one of ordinary skill in the art. For example, providing monitoring apparatus 304 and positioning the monitoring apparatus 306 as depicted in FIG. 3 may occur after delivering auditory stimulation to the subject when the subject is awake 310.

Figure 6:
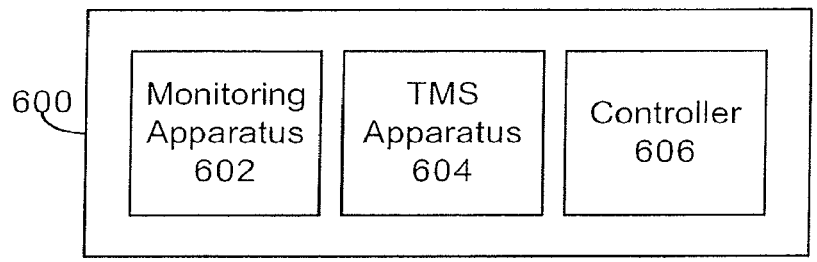
FIG. 6 is a diagrammatic representation of one exemplary transcranial magnetic stimulation system according to the present invention.

In at least another embodiment according to the present invention, the subject may self-actuate the auditory stimulations during the learning period. For example, the stimulation system may have one or more self-actuation inputs such that while a subject is learning one or more learning tasks, the subject may actuate the stimulation system to deliver one or more stimulations (e.g., auditory stimulations or olfactory stimulations). The subject may choose to deliver the same or different stimulation for each subject, fact, and/or task. For example, a subject may press a self-actuation button (or use some other actuation input such as, e.g., a touch screen, microphone, foot switch, keyboard, etc.) to deliver 10 second (same or different) auditory stimulation for each math problem that the subjects learns and may press a different self-actuation button to deliver 5 second (same or different) visual and auditory stimulation for each history fact that the subject is learning. Each stimulation that was delivered to the subject during the learning period may be stored on the stimulation system such that the stimulation system may deliver all of the stimulations that were delivered during the learning period to the subject during the sleep period. In one or more embodiments, each stimulation may be delivered during a selected stage of sleep, state of the subject, etc. as described herein FIG. 6 is a diagrammatic representation of one exemplary transcranial stimulation system 600 according to the present invention. The system 600 includes monitoring apparatus 602 and TMS apparatus 604. The monitoring apparatus 602 may be the same as or similar to the monitoring apparatus as described with reference to step 104 of the method 100 depicted in FIG. 1. The TMS apparatus may be the same as or similar to the TMS apparatus as described with reference to step 102 of the method 100 depicted in FIG. 1.

The transcranial stimulation system 600 may further include a controller 606. The controller 606 may interface with the monitoring apparatus 602 and the TMS apparatus 604. The controller 606 may be a microcontroller (e.g., PIC microcontroller), or any other electrical controller, that may include one or more central processing units, I/O ports (e.g., serial ports, USB ports), volatile memory, nonvolatile memory, clock generators, analog-to-digital converters, etc. At least one input of the controller 606 may receive data, e.g., one or more signals, from the monitoring apparatus 602. Such data may be indicative of the specific sleep stage or sleep phenomena the subject is currently undergoing, or may be simply raw data from the electrodes of the monitoring apparatus 602. The controller 606 may further include one or more self-actuation inputs for self-actuating TMS to be delivered to the subject during the learning period.

At least one output of the controller 606 may be coupled to the TMS apparatus 604 so that the controller may initiate and terminate the delivery of TMS to the subject. The controller 606 may deliver TMS to the subject based on the data it receives from the monitoring apparatus 602 as described herein with respect to the methods depicted in FIGS. 1-2.

Although not shown, the transcranial stimulation system 600 may include a power source, e.g., a battery, line source (e.g., power cord), fuel cell, etc.

Figure 7:
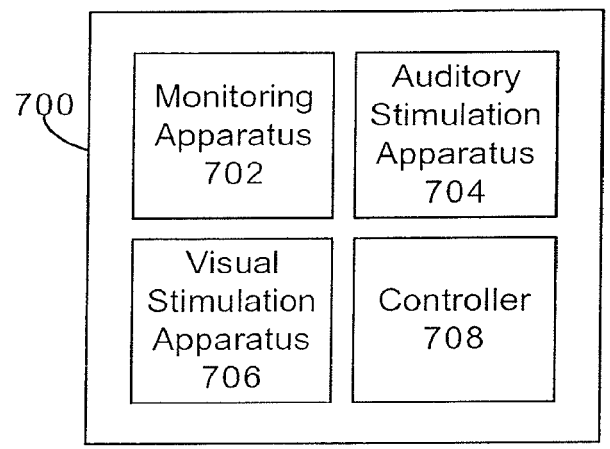
FIG. 7 is a diagrammatic representation of one exemplary auditory and/or visual stimulation system according to the present invention.

FIG. 7 is a diagrammatic representation of one exemplary auditory/visual stimulation system 700 according to the present invention. The auditory stimulation system 700 may include monitoring apparatus 702, auditory stimulation apparatus 704, visual stimulation apparatus 706, and a controller 708. The monitoring apparatus 702 may be the same as or similar to the monitoring apparatus as described with reference to step 104 of the method 100 depicted in FIG. 1. The auditory stimulation apparatus may be the same as or similar to the auditory stimulation apparatus as described with reference to step 302 of the method 300 depicted in FIG. 3. The controller 708 may be the same as or similar to the controller as described with reference to the controller 606 of system 700 depicted in FIG. 7.

The controller 708 may further include one or more self-actuation inputs such that a subject may self-actuate the auditory stimulation apparatus 704 and/or visual stimulation apparatus 706. For example, a subject may self-actuate one or more visual stimulations during each learning task the subject is learning that is associated with memory tasks. The controller 708 may record or track the visual and/or auditory stimulations delivered to the subject during the learning period such that the visual and/or auditory stimulations may be again delivered to the subject when the subject is sleep, e.g., during the appropriate stages of sleep corresponding memory consolidation.

The visual stimulation apparatus 706 may provide visual stimulation to the subject (e.g., stimulate the subject's eyes through closed eyelids). The visual stimulation apparatus 706 may be any apparatus capable of delivering visual stimulation. For example, the visual stimulation apparatus 706 may include light emitting diodes (LED), liquid crystal displays (LCD), organic light emitting diodes (OLED), incandescent light sources, electroluminescent light sources, etc. The visual stimulation apparatus 706 may include apparatus for holding the visual stimulation apparatus 706 proximate the subject's eyes (e.g., goggles, glasses, headbands, hats, etc.). Further, the visual stimulation apparatus 706 may be spaced from the subject's eyes and positioned such that it directs the visual stimulation towards the subject's eyes. The visual stimulation may be delivered such that the stimulation is receivable through the subject's eyelids for, e.g., an asleep period, or an awake period where the subject closes their eyes. The visual stimulation may include flashing lights, still images, movie clips, animations, etc. Visual stimulation may include any visible activity (typically, light having a wavelength of about 400-700 nanometers). Further, the visual stimulation, e.g., flashing lights, may vary in frequency, duration, pattern, and/or intensity.

Although not depicted, the auditory/visual stimulation system 700 may include a storage medium, e.g., flash memory, a hard drive, a CD-ROM, etc., for storing various unique auditory stimulation. Such storage memory may be removable and interchangeable as to, e.g., be programmed and/or loaded by a personal computer. Further, the auditory/visual stimulation system 700 may include an auditory output device such as, e.g., headphones, speakers, etc.

In at least one embodiment, the TMS system 600 and the auditory/visual stimulation system 700 may be combined and used in conjunction with each other utilizing, e.g., the methods described herein and depicted in FIGS. 1-5, etc. In other words, the stimulation delivered may include one or more of TMS, auditory stimulation, and/or visual stimulation. The combination of one or more of TMS, auditory stimulation, and visual stimulation may always be delivered together or they may be selectively combined. Further, the one or more of TMS, auditory stimulation, and/or visual stimulation may be delivered simultaneously and/or sequentially.

Figure 8:
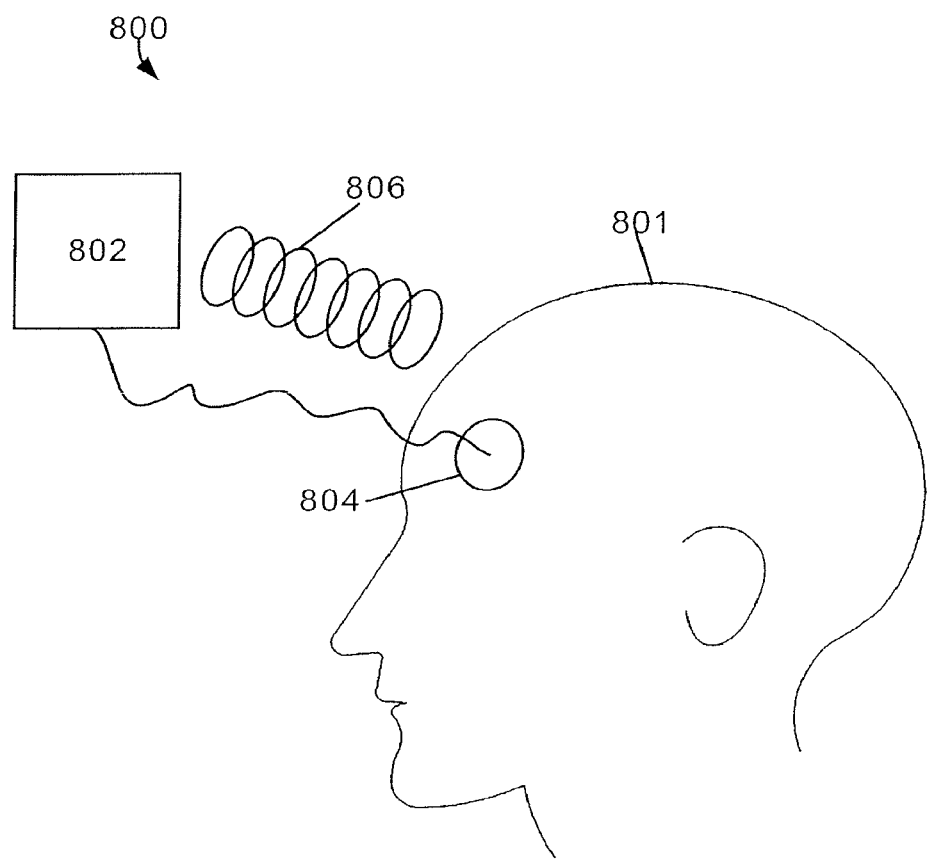
FIG. 8 is an illustrative view of one exemplary embodiment of the transcranial magnetic stimulation system according to the present invention.

FIG. 8 is an illustrative view of one exemplary embodiment of a stimulation system 800 being used with subject 801. Stimulation system 800 includes apparatus 802 that includes monitoring apparatus (e.g., EEG apparatus) and TMS apparatus. An electrode 804 is attached to the forehead of the subject 801 and is electrically coupled to the apparatus 802. The electrode 804 may transmit a signal to the apparatus 802 to, e.g., measure the electrical activity of the subject's brain. Illustrative waves 806 are shown to represent TMS that may be delivered from the apparatus 802 to the subject 801 as described herein. Further, some components that may be included in TMS systems according to the present invention may be described in U.S. Patent Application Pub. No. 2008/0081941 A1, published on Apr. 3, 2008, and entitled "Method and Apparatus for Promoting Restorative Sleep."

Figure 9A:
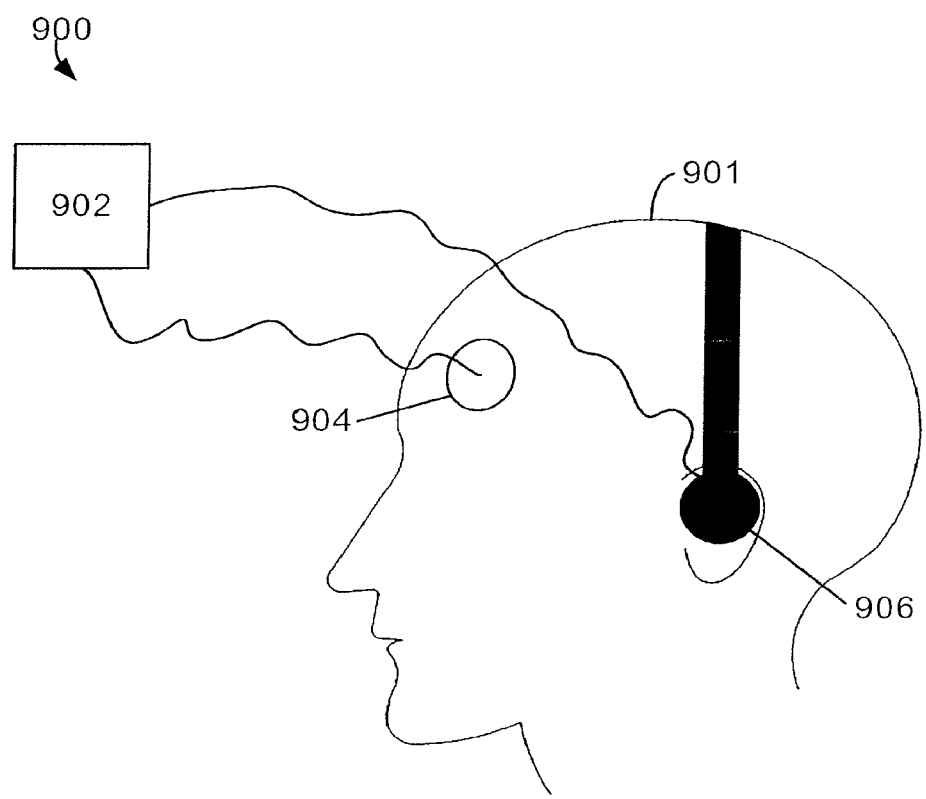
FIG. 9A is an illustrative view of one exemplary embodiment of an auditory stimulation system according to the present invention.

FIG. 9A is an illustrative view of another exemplary embodiment of a stimulation system 900 being used with subject 901. Stimulation system 900 includes apparatus 902 that includes monitoring apparatus and auditory stimulation apparatus. An electrode 904 is attached to the forehead of the subject 901 and is electrically coupled to the apparatus 902. The electrode 904 may transmit a signal to the apparatus 902 to measure, e.g., the electrical activity of the subject's brain, the muscular activity of the subject's temporalis muscle, etc. Headphones 906 are connected to the apparatus 902 and located proximate the subject's ears for delivering auditory stimulation from the apparatus 902 to the subject 901 as described herein.

Figure 9B:
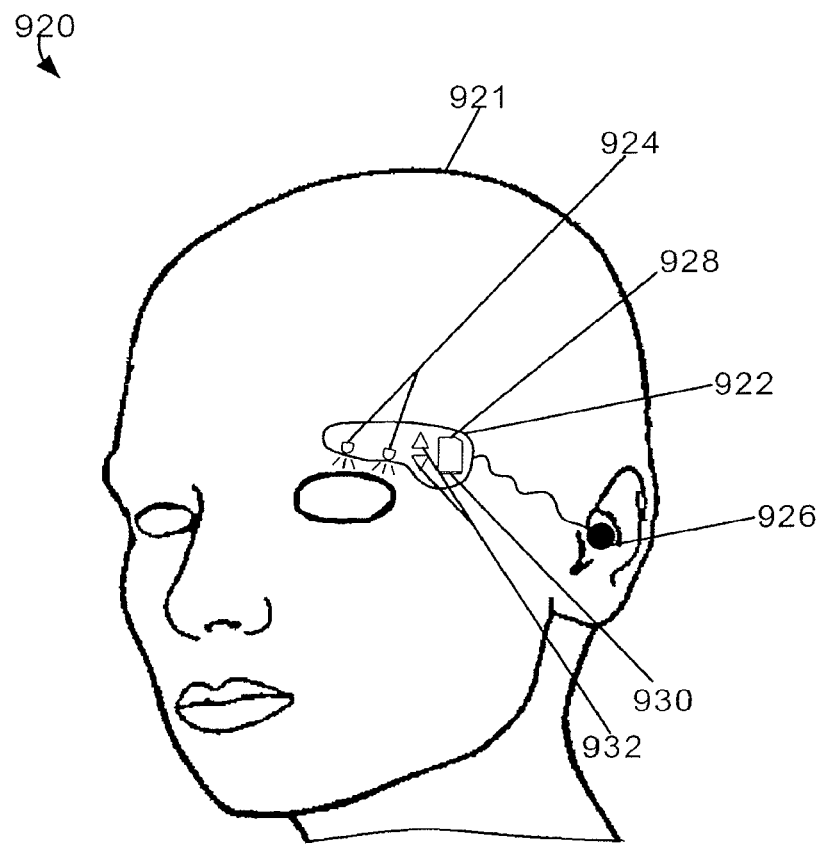
FIG. 9B is an illustrative view of one exemplary embodiment of an auditory/visual stimulation system according to the present invention.

FIG. 9B is an illustrative view of another exemplary embodiment of a stimulation system 920 being used with subject 921. Stimulation system 920 includes a stimulation patch 922 that includes monitoring apparatus, auditory stimulation apparatus, and visual stimulation apparatus. One or more electrodes may be located on the rear side (not shown—see FIG. 11 for a rear view of an exemplary stimulation patch) of the patch 922. As shown, the patch 922 is attached to the forehead of the subject 921, although other placement locations may be envisioned.

The patch 922 may be attached to the forehead of the subject 921 using adhesive on the interior surface of the patch, i.e., the surface facing the subject's forehead. The adhesive may preferably be any skin-compatible, pressure-sensitive adhesive that may adhere to a subject and that may be removed without significantly damaging the subject's skin. Further, the adhesive and/or the patch 922 may include apertures such that the patch 922 is "breathable." Also, the adhesive and/or patch 922 may be flexible so that it may conform to uneven surfaces, such as a subject's forehead. The adhesive may cover, partially cover, or not cover the electrodes. In at least one embodiment, the adhesive may be thinner over the electrodes than the remainder of the patch 922 such that sufficient conductivity can be obtained between the electrodes and the subject's skin. In at least one embodiment, the adhesive may be in the form of an adhesive pad or cushion. A non-stick, protective backing material may be located over the adhesive of the patch that may be peeled-off before attaching the patch to a subject. The patch may be able to sense when the backing material is removed from patch and thereby turn "on" the patch. Attaching the patch to a subject may include peeling a protective layer from the adhesive surface of the patch, locating the patch proximate to the portion of the subject to be monitored, and applying the patch to the portion of the subject (e.g., forehead, temple, etc.). In other embodiments, a user may apply an adhesive substance to the rear side of the patch before applying the patch to the subject.

Speaker 926 may be connected to the stimulation system 900 and located proximate the subject's ear for delivering auditory stimulation from the patch 922 to the subject 921 as described herein.

The patch of FIG. 9B also includes visual stimulation devices 924. As depicted, the visual stimulation devices 924 may be one or more light-emitting devices (such as, e.g., a pair of light-emitting diodes). The visual stimulation devices 924 may emit one or more colors of light of varying brightness, frequency, intensity, etc.

The patch 922 may further include a memory device slot 928 and a memory device 930. The memory device 930 may be any non-volatile storage device. It may be preferred that the memory device 104 be in the form of a flash memory device, such as, e.g., Compact Flash (CF), MultiMedia Card (MMC), Secure Digital (SD), Memory Stick, xD, RS-MMC, miniSD, microSD, Intelligent Stick, etc. In other embodiments, the system may include a non-removable storage device. Further, in at least another embodiment, the system may include a volatile storage device.

The memory device slot 928 may be a slot designed to receive the memory device 930. When the memory device 930 is inserted into the memory device slot 928 (as shown), the electrical contacts of the memory device 930 may contact the electrical contacts of the memory device slot 928 to allow communication between the memory device and other componentry of the system 920. In at least one embodiment, the memory device 930 may fit within the memory device slot 928 with an interference fit. Further, in at least another embodiment, the slot 928 may include a latch or another retention device for securing the memory device 930 within the slot 928.

The memory device slot 928 may be electrically coupled to the electronic componentry of the system 920 such that data may be stored on the memory device 930. As described herein, "electrically coupled" may be any electrical connection, e.g., using a conductive material such as wire connection, flexible circuit board, printed circuit board, etc.

The stimulation patch 920 may further include one or more input buttons 932. A user may depress the input buttons 932 to perform a variety of features with the stimulation system 920. For example, a user may user the input buttons 932 to enable or disable various components of the stimulation system (e.g., auditory stimulation apparatus, visual stimulation apparatus, monitoring apparatus, etc.), alter various parameters of the monitoring apparatus (e.g., sensitivity, sampling rate, filters, etc.), change the auditory stimulation being delivered, electronically mount or un-mount the memory device, alter various parameters of the auditory stimulation (e.g., volume, frequency, bass, treble, etc.), alter various parameters of the visual stimulation (e.g., pattern, intensity, color, duration, brightness, frequency, etc.), etc. In the embodiment depicted in FIG. 9B, the buttons are triangular shaped to, e.g., indicate up and down arrows. In other embodiments, however, the buttons may be multiple shapes and sizes. Further, in other embodiments, the system 920 and/or patch 922 may include multiple buttons (e.g., three or more buttons). Further, although this embodiment depicts depressible buttons, input buttons according to the present invention may be any input device, e.g., switches, toggles, touch screens, etc.

Although not depicted, the stimulation system 920 may further include other componentry that may be required to monitor the state of the subject and deliver auditory and/or visual stimulation to the subject including, e.g., electronic apparatus, power switches, power sources, indicator lights, etc.

The one or more input buttons 932 may be self-actuation inputs. Self-actuation inputs may be used to deliver one or more stimulations to the subject at the subject's control. For example, the subject may depress one of the input buttons 932 to deliver a unique auditory stimulation (e.g., a 5 second tone). The stimulation system 920 may then record what auditory stimulations were delivered during the learning period such that they may be delivered to the subject while the subject is sleeping, e.g., during a specific sleep stage. The self-actuation inputs may further be utilized to change the type of auditory stimulation or type of stimulation (auditory, visual, etc.) to be delivered. For example, a subject may be utilizing auditory stimulations consisting of classical music for history memorization problems and upon switching to learning Spanish language study may want to change the auditory stimulations to ambient noise (e.g., water gurgling) or may want to change to visual stimulations (e.g., faint blue light).

For example, stimulation system may be turned "on" using a power switch that may be any kind of two or more position switch. The power switch may be electrically coupled to electronic apparatus, a power supply, etc. The power switch may have more than two positions for different modes of operation of the stimulation system. For example, the power switch may have three positions: "awake," "asleep," and "off." When the power switch is in the "awake" position, the stimulation system may be capable of delivering auditory stimulation the subject either automatically (e.g., the system may automatically deliver auditory stimulation), semi-automatically (e.g., the system may automatically deliver auditory stimulation and the user may manually change the type of auditory stimulation), and/or manually (e.g., the user may start and stop the auditory stimulation and may change type of auditory stimulation). When the power switch is in the "asleep" position, the stimulation system may monitor the state of the subject and deliver auditory stimulation when the subject is in the proper state. When the power switch is in the "off" position, the stimulation patch may be dormant.

Further, for example, the power switch may have a position for a "download" mode in which data may be transferred to and from the stimulation system. Also, in other embodiments, the stimulation patch may be turned "on" by attaching the patch to a subject's forehead (e.g., the patch may include electrodes capable of sensing when the patch is contacting skin—at which time, apparatus on the patch may be turned "on").

Also, the stimulation patch may further include an indicator light. The indicator light may be a single LED. In at least one embodiment, however, the indicator light may consist of one or more LEDs, OLEDs, and/or LCDs. The indicator light may indicate to the user the mode or state of the stimulation patch. For example, if the indicator light is "on," then the indicator light may be indicating that the stimulation patch is monitoring, e.g., EEG signals from the electrodes and storing such signals on the memory device. Also, for example, the indicator light may "blink" to indicate the power source is running low on power.

Figure 9C:
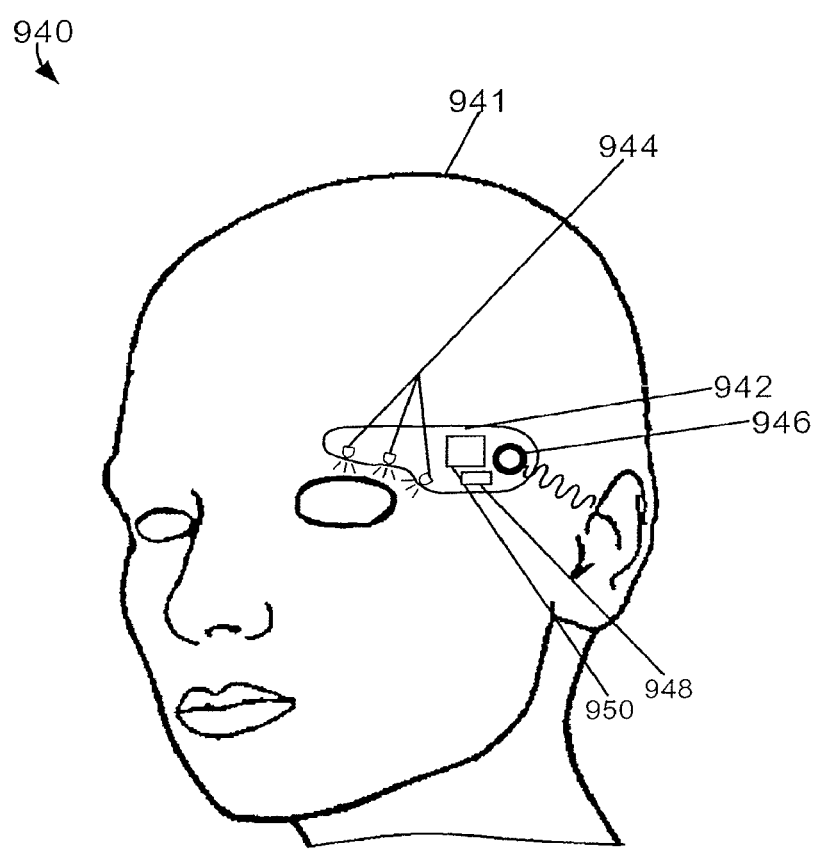
FIG. 9C is an illustrative view of another exemplary embodiment of an auditory/visual stimulation system according to the present invention.

FIG. 9C is an illustrative of view of another exemplary embodiment of a stimulation system 940 being used with subject 941. Stimulation system 940 includes a stimulation patch 942 that includes monitoring apparatus, auditory stimulation apparatus, and visual stimulation apparatus. One or more electrodes may be located on the rear side (not shown) of the patch 942. As shown, the patch 942 is attached to the forehead of the subject 941 using, e.g., adhesive.

The patch further includes one or more visual stimulation devices 944 similar to those described with respect to the embodiment depicted in FIG. 9B.

The stimulation patch 942 further includes power source 948 and electronic apparatus 950. The power source 948 may be a watch battery, fuel cell, etc. The electronic apparatus 950 may include a microcontroller, microprocessors, EEG apparatus, EMG apparatus, EOG apparatus, power management units, analog-to-digital converters, digital signal processors, input/output (I/O) ports, etc. The electronic apparatus 950 may include an I/O port that is electrically coupled to, e.g., a memory device slot. Such electrical coupling may be in the form of any suitable interface, e.g., serial data connection, parallel data connection, Advanced Technology Attachment (ATA), Small Computer System Interface (SCSI), Serial Advanced Technology Attachment (SATA), Universal Serial Bus, IEEE 1394, etc. Further, such electrical coupling may be utilized to couple the stimulation patch 942 to a configuration apparatus, e.g., a personal computer.

The monitoring apparatus may be integrated with the electronic apparatus 950 on a single microchip. In other embodiments, the electronic and/or monitoring apparatus may include multiple electronic components electrically coupled to each other on, e.g., a printed circuit board. In at least one embodiment, the electronic apparatus including monitoring apparatus may be attached to a flexible circuit board. The I/O ports of the monitoring apparatus may be electrically coupled to the one or more electrodes. The one or more electrodes may transmit an electrical signal. The electrical signal may be an analog signal which may be converted to digital data with an analog-to-digital converter. Digital data representative of the analog signal may be stored on, e.g., a memory device. In other embodiments, an analog signal from the one or more electrodes may be stored on a storage apparatus, e.g., magnetic tape, etc.

The stimulation patches according to the present invention may be described as being "self-contained." As used herein, a self-contained stimulation patch may be defined as having all parts necessary for its operation (e.g., monitoring apparatus, apparatus, electronic apparatus, etc.) located within or on the patch itself (e.g., the substrate of the patch).

The auditory stimulation apparatus of the stimulation system 940 may include a speaker 946 as shown emitting "sound waves" in FIG. 9C. Although this embodiment only includes a single speaker, the stimulation systems according to the present invention may include two or more speakers. In at least one embodiment, the stimulation system includes a patch that when attached a subject extends across the subject's forehead from the left temporalis muscle to the right temporalis muscle and includes a speaker at either end of the patch for emitting auditory stimulation to each ear (e.g., patch 1150 depicted in FIG. 12).

Although the embodiments described above utilize either TMS apparatus, visual stimulation apparatus, and/or auditory stimulation apparatus, the methods and/or systems according to the present invention may utilize any other type of stimulation apparatus in place of or in addition to TMS apparatus, visual stimulation apparatus, and/or auditory stimulation apparatus. Further, each component of the systems depicted in FIGS. 9A-9C may be utilized on any of the systems depicted in FIGS. 9A-9C (although not necessarily shown or described with reference to that particular system).

Figure 10:
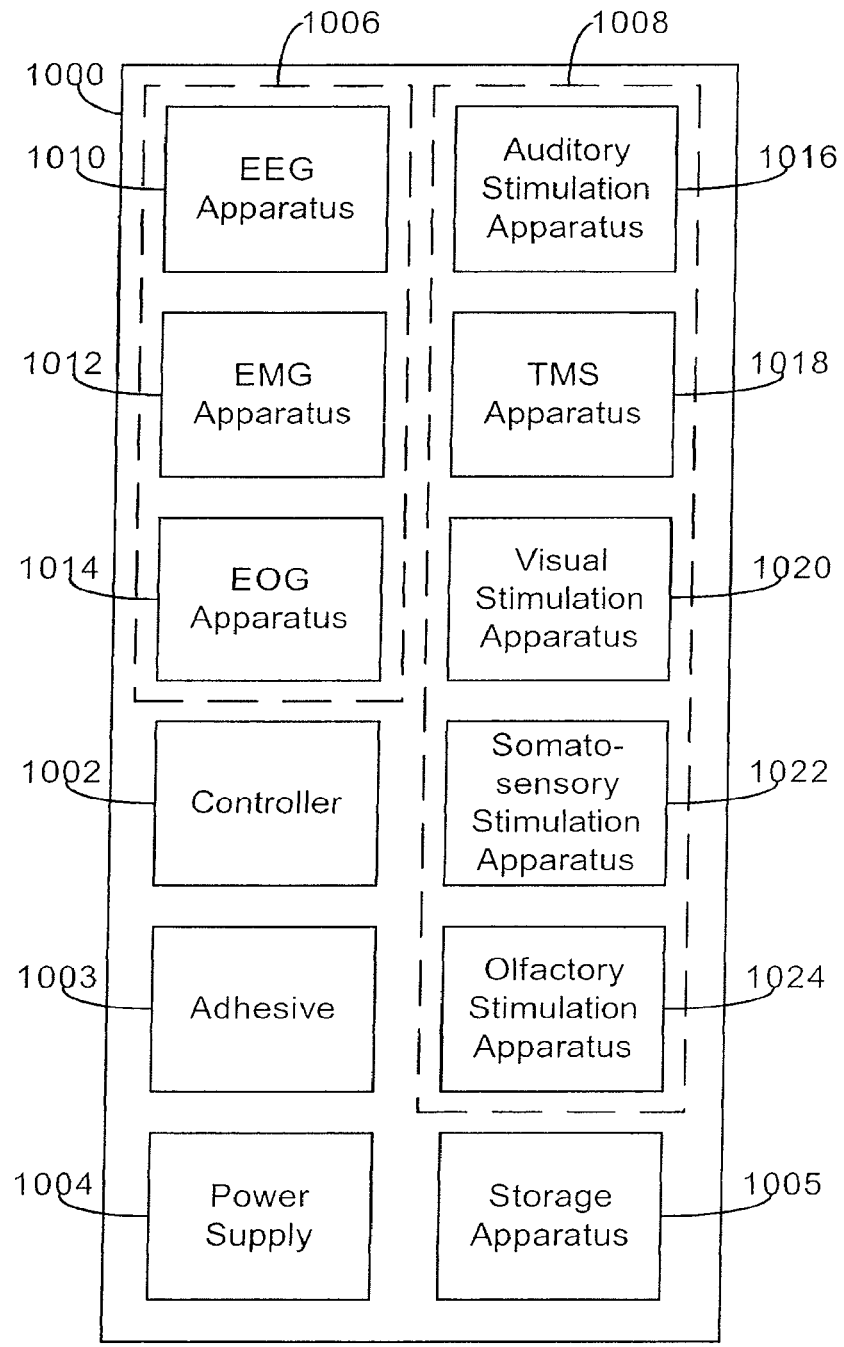
FIG. 10 is a diagrammatic representation of one exemplary stimulation system according to the present invention.

FIG. 10 is a diagrammatic representation of one exemplary stimulation system 1000 that includes a controller 1002, adhesive 1003 (e.g., to attach a stimulation patch to a subject), a power supply 1004, storage apparatus 1005, monitoring apparatus 1006, and stimulation apparatus 1008.

The monitoring apparatus 1006 includes EEG apparatus 1010, EMG apparatus 1012, and/or EOG apparatus 1014. Each of the monitoring apparatus may include one or more electrodes to be locate adjacent the subject to monitor various parameters that may indicate when the subject is in the proper state for stimulation to be delivered to the subject.

The EEG apparatus 1010 may include microcontrollers, microprocessors, analog-to-digital converters, digital signal processors, I/O ports, etc. The EEG apparatus 1010 may be capable of recording the neural activity of electrical potential across cell membranes. The changes in electrical potential in the cortex contain rhythmical activity, which typically occur at frequencies of about 0.5 hertz to about 70 hertz. The EEG apparatus 1010 may continuously sample the neural activity of the subject at about 100 hertz or less, 60 hertz or less, etc. and may monitor the neural activity of the subject that oscillates between about 0.5 hertz or more, about 70 hertz or less, etc. In at least one embodiment, the EEG apparatus 1010 may monitor the neural activity of the subject that oscillates between about 0.5 hertz to about 70 hertz. Also, the EEG apparatus 1010 may monitor the neural activity of the subject at selected intervals, e.g., 1 minute for every 5 minutes or 15 seconds for every 1 minute.

The EMG apparatus 1012 may include microcontrollers, microprocessors, analog-to-digital converters, digital signal processors, I/O ports, etc. The EMG apparatus 1012 may be capable of recording the muscular activity of electrical potential across muscular membranes. Changes in electrical potential in muscular membranes may oscillate between about 10 hertz or more, about 90 hertz or less, etc. depending on the size of the muscle, the type of muscle, etc. The EMG apparatus 1012 may sample the muscular activity of the subject at about 180 hertz or less, about 100 hertz or less, etc., and may monitor the muscular activity of the subject that oscillates at about 0.5 hertz or more, about 10 hertz or more, about 90 hertz or less, about 180 hertz or less, etc. Further, the rate at which the EMG apparatus 1012 may sample the muscular activity of the subject may be selectable by, e.g., a switch or an administrator prior to attaching the stimulation patch. In at least one embodiment, the EMG apparatus 1012 may monitor the muscular activity of the temporalis muscle and/or frontalis muscle of a subject that corresponds to REM sleep, e.g., the muscular activity of the temporalis muscle and/or frontalis muscle that oscillates at about 10 hertz or more, about 90 hertz or less, etc. Further, the EMG apparatus 1012 may measure electrical potential at about 25 microvolts or more, about 50 millivolts or less, etc.

The EOG apparatus 1014 may include microcontrollers, microprocessors, analog-to-digital converters, digital signal processors, I/O ports, etc. The EOG apparatus 1014 may be capable of recording the ocular activity of a subject. Changes in electrical potential near the subject's eye as a result of ocular activity may oscillate between about 0.5 hertz and about 200 hertz. The EOG apparatus 1014 may sample the ocular activity of the subject at about 180 hertz or less, about 100 hertz or less, etc., and may monitor the ocular activity of the subject that oscillates at about 0.5 hertz or more, about 2 hertz or more, about 100 hertz or less, about 200 hertz or less, etc. Further, the rate at which the EOG apparatus 1014 may sample the ocular activity of the subject may be selectable by, e.g., a switch or an administrator prior to attaching the stimulation system. EOG monitoring may be limited to periods when the EEG apparatus and/or EMG apparatus indicate that a subject is sleeping.

The stimulation apparatus 1008 may include auditory stimulation apparatus 1016, TMS apparatus 1018, visual stimulation apparatus 1020, somatosensory stimulation apparatus 1022, and/or olfactory stimulation apparatus 1024. The auditory stimulation apparatus 1016, the TMS apparatus 1018, and the visual stimulation apparatus 1020 may be substantially similar to the auditory stimulation apparatus, TMS apparatus, and visual stimulation apparatus as previously described herein.

The somatosensory stimulation apparatus 1022 may physically stimulate a subject (e.g., stimulate a subject's arm). The somatosensory stimulation apparatus 1022 may include vibratory apparatus, compression apparatus, acupuncture apparatus, thermal apparatus (heating and/or cooling), etc. The somatosensory stimulation apparatus 1022, however, may be any apparatus capable of delivering any type of somatosensory stimulation. The somatosensory stimulation apparatus 1022 may be located anywhere proximate the subject's body such that it may deliver somatosensory stimulation to the subject. In at least one embodiment, the somatosensory apparatus 1022 may be a sleeve that may be positioned around an appendage (e.g., arm, leg, finger, etc.) of the subject. Further, the somatosensory apparatus 1022 may be spaced away from subject such that only the actual somatosensory stimulation contacts the subject (e.g., warm air). The somatosensory stimulation may include vibrations, compressions, warm air, cool air, humid air, electrical current, pinching, rubbing, etc. In at least one embodiment, the somatosensory stimulation, e.g., compressions and/or vibrations, may vary in frequency, duration, pattern, and/or intensity.

The olfactory stimulation apparatus 1024 may provide aromatic stimulation a subject by, e.g., delivering one or more scents to the subject. The olfactory stimulation apparatus 1024 may be located anywhere proximate the subject's body such that it may effectively deliver the olfactory stimulation to the subject. In at least one embodiment, the olfactory apparatus 1024 may be worn around the subject's neck. Further, the olfactory apparatus 1024 may be spaced away from subject (i.e., the olfactory apparatus 1024 does not contact the subject) such that only the actual olfactory stimulation contacts the subject (e.g., the olfactory apparatus may be similar to an air freshener plugged into an outlet of a wall). Also, one or more distinct scents may be provided by the olfactory stimulation apparatus 1024.

The stimulation delivered from the stimulation apparatus 1008 may be delivered during a selected time period, during one or more selected time periods, or continuously. Further, the stimulation apparatus 1008 may deliver stimulation at different time periods from one another. In at least one embodiment, the delivery of stimulation while the subject is awake may only occur while the subject is learning a specific task. Such learning may include memorization, reading and comprehension, motor skills, verbal fluency, any other learning paradigm, etc. Further, the delivery of stimulation while the subject is awake may only occur when the electrical activity in the subject's brain indicates that the subject is in a particular state. For example, as described herein, one such state may be when a subject's hippocampal brainwaves are operating in the theta frequency (or any other selected frequency range).

Also, the stimulation may be delivered to the subject when the subject is asleep during a selected time period, during one or more selected time periods, or continuously. The delivery of the stimulation while a subject is both awake and asleep may create an association between the learning task and/or tasks that the subject experienced during the awake period and the memory consolidation of such learning task or tasks during sleep.

The controller 1002 may include multiple inputs, e.g., self-actuation inputs. The self-actuation inputs may allow a subject to self-actuate the delivery of unique stimulation (e.g., auditory, visual, olfactory, somatosensory, or transcranial magnetic stimulation) to the subject as described herein.

The controller 1002, adhesive 1003 (e.g., to attach a stimulation patch to a subject), a power supply 1004, storage apparatus 1005, monitoring apparatus 1006, and stimulation apparatus 1008 may be a single, integral unit, or may be multiple interconnected units. Further, the stimulation apparatus 1008 and/or monitoring apparatus 1006 may be used in accordance with any method described herein including the methods depicted in FIGS. 1-5. Such methods include delivering stimulation to a subject when the subject is determined to be undergoing a specific portion of the sleep cycle, delivering stimulation to a subject for a selected time period, delivering stimulation to subject when the electrical activity of the subject's brain is undergoing a specific frequency, etc.

Furthermore, each of the stimulation apparatus 1008 and other apparatus, systems, and methods described herein may be used any combination whatsoever. For example, a stimulation system according the present invention may include a controller, a power system, electroencephalography apparatus, TMS apparatus, and olfactory apparatus.

Figure 11:
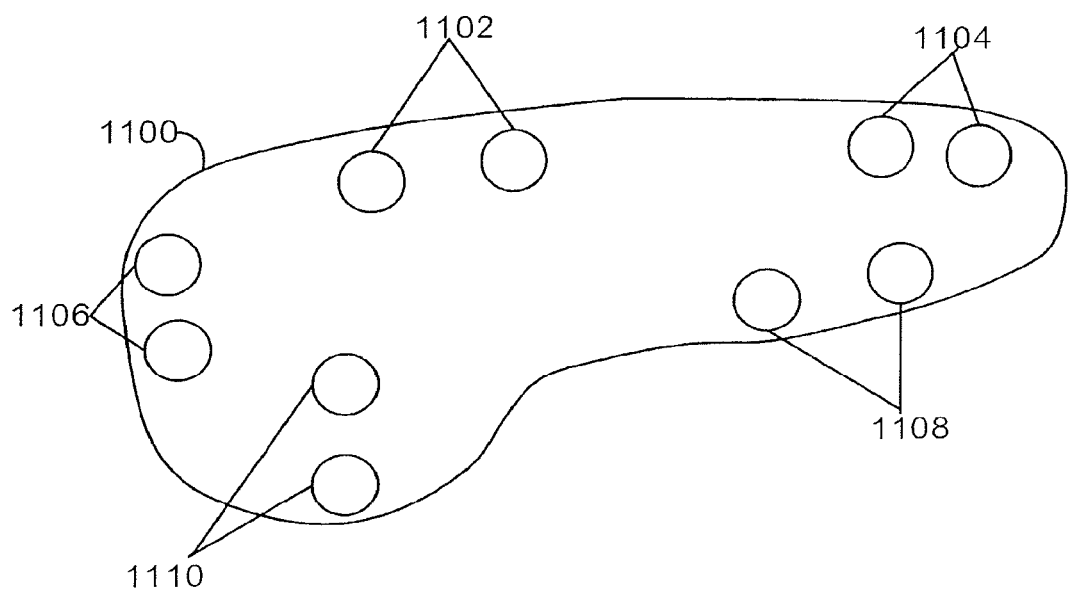
FIG. 11 is an illustrative view of the stimulation system of FIG. 9B.

A rear view of a stimulation patch 1100 is depicted in FIG. 11. The stimulation patch 1100 may be similar to the stimulation patch 922 depicted in FIG. 9B. This view shows the electrodes of the stimulation patch 1100. For example, stimulation patch 1100 includes monitoring apparatus having EEG electrodes 1102 located to correspond to a subject's temporal lobes, EEG electrodes 1104 located to correspond to a subject's frontal lobes, EMG electrodes 1106 located to correspond to a subject's temporalis muscle, EOG electrodes 1108 located to correspond to a subject's ocular cavity, and reference electrodes 1110. Further, the stimulation patch 1100 may include EEG, EMG, and EOG apparatus (although not depicted) to monitor and collect data from the electrodes. Since FIG. 11 depicts the rear view of a stimulation patch, i.e., the surface that will be adhered to the subject, the surface may include adhesive.

Although multiple electrodes are depicted for each type or class, only one electrode may be required at each location. The use of multiple electrodes provides redundancy (if, e.g., an electrode loses contact, an electrode malfunctions, etc.). Also, any of the electrodes on the patch may be used as a reference electrode (if, e.g., the use of a different electrode provides a better reference signal, a reference electrode malfunctions, etc.).

Figure 12:
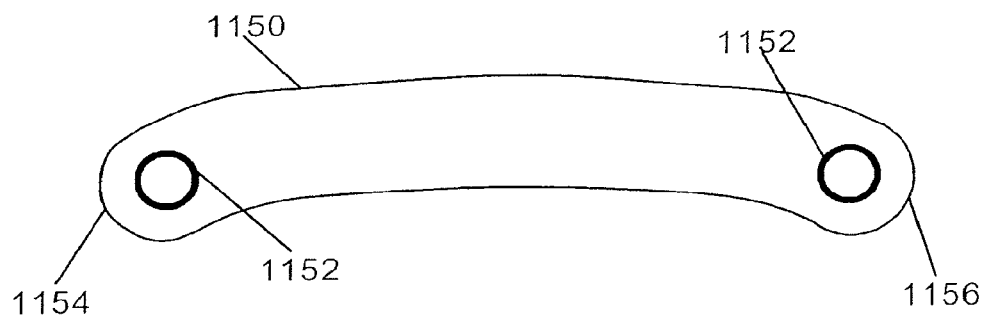
FIG. 12 is an illustrative view of one exemplary embodiment of a stimulation system according to the present invention.

A front view of a stimulation patch 1150 is depicted in FIG. 12. Stimulation patch 1150 may be similar to the stimulation patches described herein except that the stimulation patch 1150 may sized and shaped to extend across the forehead of a subject from a first end 1154 to a second end 1156. Each end 1154, 1156 may correspond to a subject's temporalis muscle (e.g., to be monitored by monitoring apparatus having electrodes located at either end 1154, 1156) and may include an auditory stimulation output device, e.g., a speaker 1152. In at least one embodiment, the patch 1150 may include multiple electrodes located throughout the patch 1150 to monitor any portion of the subject's head.

Figure 13:
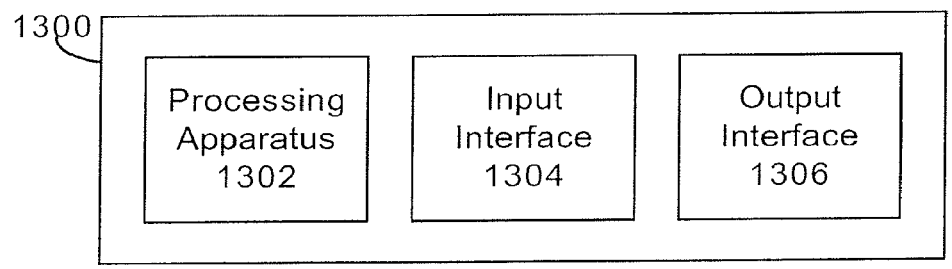
FIG. 13 is a diagrammatic representation of one exemplary configuration apparatus according to the present invention.

FIG. 13 is a diagrammatic representation of one exemplary embodiment of a configuration system 1300 according to the present invention. The configuration system 1300 may be utilized by a user to analyze to program and/or configure the stimulation systems described herein. A user may utilize the configuration system 1300 to configure the stimulation system with specific "play" lists, genres (e.g., jazz, hip-hop, classical, etc.), auditory types (e.g., ambient noise, white noise, etc.), visual stimulation parameters, olfactory stimulation parameters, somatosensory stimulation parameters, etc. Such configuration may further include uploading auditory stimulation, e.g., digital music files, to the stimulation system.

In at least one embodiment, the user may select the type of stimulation (e.g., auditory, transcranial magnetic, visual, olfactory, or somatosensory stimulation) to correspond to each different type of learning task using the configuration apparatus. As such, the user may merely select a learning task on the stimulation system (e.g., patch) and the system may automatically deliver the stimulation the user already selected to correspond to the learning task. Further, a set of stimulations may be selected to correspond to each learning task such that each sub-task (e.g., each problem of a set of math problems) may have a unique stimulation. After a set of stimulations is selected to each learning task, a user may select the learning task and upon beginning each sub-task, the user may self-actuate to deliver one of the set of stimulations corresponding to the learning task. Furthermore, a user may be able change learning tasks during the learning period such that a different stimulation or set of stimulations corresponding to the new learning task may be delivered through, e.g., self-actuation.

The configuration system 1300 may include a processing apparatus 1302, an input interface 1304, an output interface 1306, and a power supply (not depicted). The configuration system 1300 may be a personal computer running an operating system such as Microsoft Windows, GNU/Linux, Apple OS X, etc. In other embodiments, the configuration system 1300 may be a personal data assistant (PDA), a laptop computer, a cellular telephone, an ultra-mobile personal computer (UMPC), etc.

The input interface 1304 may be an interface designed to receive the data recorded the monitoring apparatus of the stimulation systems described herein. Further, the input interface 1304 may include a slot for receiving a removable memory device such as the memory device 930 of FIG. 9B. In other embodiments, the input interface 1304 may be an I/O port such as a serial data port, a parallel, data port, a USB data port, etc. that may be connectable to the storage device of the stimulation patch and/or any input peripheral (e.g., mouse, keyboard, touch screen, etc.) for use a by a user. In these embodiments, a data transmission cable (e.g., a USB cable) may be connected to the input interface 1304 of the configuration system 1300 and to the stimulation system to configure the stimulation system.

The output interface 1306 may be any display, e.g., a liquid crystal display, cathode ray tube display, etc., that may be capable of displaying a configuration menu to a user to configure the stimulation system using the configuration apparatus 1304.

Figure 14:
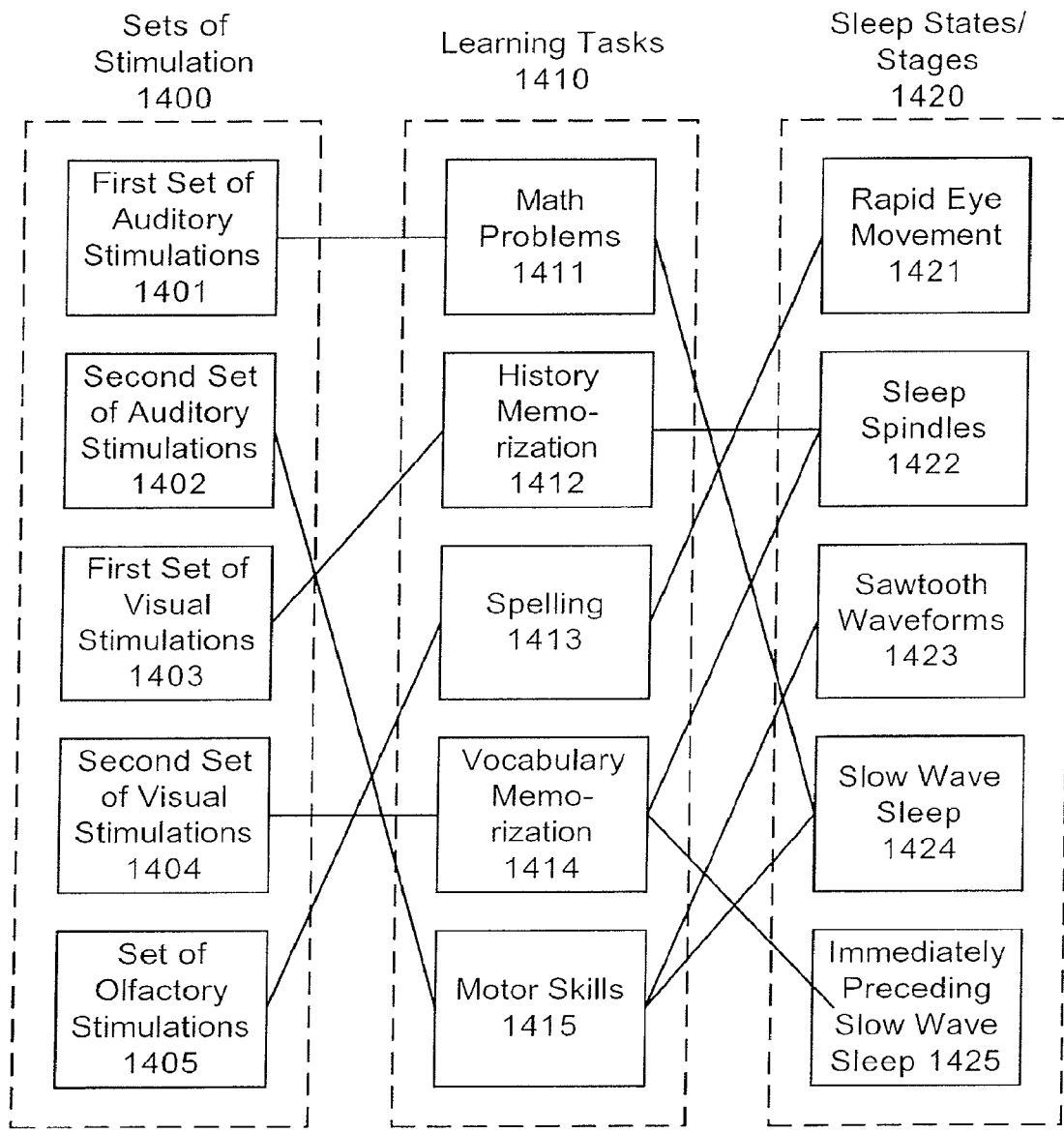
FIG. 14 is a diagrammatic representation of a configuration of a stimulation system according to the present invention.

FIG. 14 is a diagrammatic representation of a configuration of a stimulation system. The representation shows sets of stimulation 1400, learning tasks 1410, and sleep states/stages 1420. Each set of the sets of stimulation 1400 may be associated with one or more of the learning tasks 1410. Each learning task of the learning tasks 1410 may be associated with one or more sleep states/stages 1420.

For example, the first set of auditory stimulations 1401 may be associated with math problems 1411. The first set of auditory stimulations 1401 may include one or more auditory stimulations (e.g., that a user may self-actuate to deliver an auditory stimulation from the first set of auditory stimulations for each math problem during the awake period). Every auditory stimulation delivered to the subject during the awake, learning period may then be associated with slow wave sleep 1424 such that when a subject undergoes slow wave sleep, one or more of the auditory stimulations (from the auditory stimulations delivered during the awake period) may be delivered to the subject, e.g., consecutively, etc.

Further, for example, the second set of visual stimulations 1404 is associated with vocabulary memorization 1414. The second set of visual stimulations 1404 may include one or more visual stimulations (e.g., that a user may self-actuate to deliver a visual stimulation from the second set of visual stimulations for each word studied during the awake period). Every visual stimulation delivered to the subject during the awake, learning period may then be associated with sleep spindle 1422 and the period immediately preceding slow wave sleep 1425 such that when a subject undergoes sleep spindles or the period immediately preceding slow wave sleep, one or more of the visual stimulations (from the visual stimulations delivered during the awake period) may be delivered to the subject, e.g., consecutively.

Although FIG. 14 is merely a diagrammatic representation of one exemplary configuration of the stimulation systems as described herein, a user interface (e.g., run by a computer program) on configuration system 1300 as described herein reference to FIG. 13 may look similar to the diagrammatic representation in FIG. 14. A subject may use such user interface (e.g., using any input device such as a touch screen, mouse, keyboard, etc.) to select the set of stimulations to correspond to each learning task, and the learning tasks to correspond to each sleep state/stage. Further, such user interface may include the individual stimulations of the set of stimulations so that a subject may even further specifically tailor the stimulation system.

For example, a subject may have noticed while learning history that the subject has a difficult time remembering the date of the forming of the United Nations. As such, the subject may use the configuration system and user interface to deliver the stimulation that was delivered while the subject was learning the date of the forming of the United Nations during two or more sleep states/stages (while leaving rest of the stimulations corresponding to each history fact to be delivered during only one sleep state/stage).

FIG. 15 is a diagrammatic representation of one exemplary embodiment of a stimulation system 1500 according to the present invention. The stimulation system 1500 may include a learning component 1510 and a consolidation component 1520. The learning component 1510 may include TMS apparatus 1511, auditory stimulation apparatus 1512, visual stimulation apparatus 1513, olfactory stimulation apparatus 1514, somatosensory stimulation apparatus 1515, and one or more self-actuation buttons 1516. The consolidation component 1520 may include TMS apparatus 1521, auditory stimulation apparatus 1522, visual stimulation apparatus 1523, olfactory stimulation apparatus 1524, somatosensory stimulation apparatus 1525, a controller 1526, and monitoring apparatus 1527.

The learning component 1510 may be utilized by a subject during a learning period while the consolidation component 1520 may be utilized by a subject during a sleeping period. Both the learning component 1510 and consolidation component 1520 may be similar to any apparatus and/or system described herein and further may utilize any method described herein.

Although the learning component 1510 and the consolidation component 1520 are part of the stimulation system 1500, the learning component 1510 may be a component of a first unit and consolidation component 1520 may be a component of a second unit different and separate from the first unit. In this embodiment, a subject can utilize the learning component 1510 without the consolidation component 1520 during the learning period. Likewise, the subject can utilize the consolidation component without the learning component 1520 during the sleeping period. Further, in other embodiments, the learning component 1510 and the consolidation component 1520 may be components of a single integral unit.

The complete disclosure of the patents, patent documents, and publications cited in the Description of Exemplary Embodiments, and elsewhere herein are incorporated by reference in their entirety as if each were individually incorporated.

Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A stimulation system for stimulating a subject, the system comprising:
   a learning component and a consolidation component, wherein the learning component comprises:
      learning auditory stimulation apparatus for delivering an auditory stimulus selected by the subject to the subject while the subject is awake and learning a specific task; and
      one or more self-actuation input devices operably coupled to the learning auditory stimulation apparatus and configured for self-actuation by the subject to deliver the selected auditory stimulus from the learning auditory stimulation apparatus to the subject when the subject is awake and learning the specific task;
   and wherein the consolidation component comprises:
      monitoring apparatus for monitoring the sleep state of the subject while the subject is asleep;
      consolidation auditory stimulation apparatus for delivering the selected auditory stimulus to the subject; and
      a controller operably coupled to the monitoring apparatus to receive input regarding the sleep state of the subject from the monitoring apparatus and operably coupled to the consolidation auditory stimulation apparatus to operate the consolidation auditory stimulation apparatus, wherein the controller utilizes the input from the monitoring apparatus to determine when the subject is in a particular sleep state, and further wherein the controller operates the consolidation auditory stimulation apparatus to deliver the selected auditory stimulus to the subject during the particular sleep state, the particular sleep state being selected based on the specific task being learned by the subject while the subject was awake.

2. The stimulation system of claim 1, wherein the learning component and the consolidation component are components of a single integral unit.

3. The stimulation system of claim 1, wherein the learning component is a component of a first unit, wherein the consolidation component is a component of a second unit, and wherein the second unit is separate from the first unit.

4. The stimulation system of claim 1, wherein the monitoring apparatus comprises electroencephalography apparatus.

5. The stimulation system of claim 1, wherein the monitoring apparatus comprises electromyography apparatus.

6. The stimulation system of claim 1, wherein the monitoring apparatus comprises electrooculography apparatus.

7. The stimulation system of claim 1, wherein the stimulation system further comprises a self-contained patch and adhesive to attach the self-contained patch to the subject, wherein the monitoring apparatus, the consolidation auditory stimulation apparatus, and the controller are located on the self-contained patch.

8. The stimulation system of claim 1, wherein the learning auditory stimulation apparatus and the consolidation component comprise:
   memory for storing one or more selected auditory stimulations; and
   one or more output devices, wherein the one or more output devices deliver the one or more selected auditory stimulations.

9. The stimulation system of claim 1, wherein the stimulation system further comprises a configuration apparatus to configure the stimulation system, wherein the configuration apparatus comprises:
   processing apparatus;
   a first input interface coupled to the processing apparatus to receive input from the subject; and
   an input/output interface coupled to the processing apparatus to transmit data to the controller of the stimulation system.

10. The stimulation system of claim 1, wherein the learning auditory stimulation apparatus of the learning component and the consolidation auditory stimulation apparatus of the consolidation component are the same apparatus.

11. The stimulation system of claim 1, wherein the learning auditory stimulation apparatus of the learning component is different than the consolidation auditory stimulation apparatus of the consolidation component.

12. The stimulation system of claim 1, wherein the monitoring apparatus is configured for detecting electroencephalography activity using one or more electrodes.

13. A method of stimulating a subject's brain, the method comprising:
   providing auditory stimulation apparatus for delivering to a subject an auditory stimulus selected by the subject;
   providing monitoring apparatus to monitor the state of the subject;
   positioning the auditory stimulation apparatus where the subject can hear the auditory stimulations;
   delivering the selected auditory stimulus from the auditory stimulation apparatus to the subject during one or more first periods when the subject is awake and learning a specific task, wherein the selected auditory stimulus is delivered in response to self-actuation of a self-actuation input device operably coupled to the auditory stimulation apparatus, wherein the self-actuation input device is self-actuated by the subject when the subject is awake and learning the specific task; and
   delivering the selected auditory stimulus from the auditory stimulation apparatus to the subject during one or more second periods when the subject is asleep, the one or more second periods being identified by the monitoring apparatus and being selected based on the specific task being learned by the subject when the subject was awake.

14. The method of claim 13, wherein the selected auditory stimulus is selected based on the specific task being learned.

15. The method of claim 13, wherein the monitoring apparatus comprises electroencephalography apparatus to measure electrical activity of the subject's brain.

16. The method of claim 15, wherein electrical activity of the subject's brain indicative of sawtooth waveforms before rapid eye movement occurs during each of the one or more second periods.

17. The method of claim 15, wherein electrical activity in the subject's brain indicative of slow wave sleep occurs during each second period of the one or more second periods.

18. The method of claim 15, wherein electrical activity in the subject's brain indicative of an increase in slope of a waveform of the electrical activity occurs during each second period of the one or more second periods.

19. The method of claim 15, wherein electrical activity in the subject's brain indicative of an impending increase in slope of a waveform of the electrical activity occurs during each second period of the one or more second periods.

20. The method of claim 15, wherein electrical activity in the subject's brain indicative of sleep spindles occurs during each second period of the one or more second periods.

21. The method of claim 15, wherein electrical activity in the subject's brain indicative of stage II sleep immediately preceding rapid eye movement occurs during each second period of the one or more second periods.

22. The method of claim 13, wherein rapid eye movement of the subject occurs during each second period of the one or more second periods.

23. The method of claim 13, wherein the method comprises delivering the selected auditory stimulations to the subject during a plurality of the second periods when the subject is asleep.

* * * * *